(12) United States Patent
Kondo et al.

(10) Patent No.: US 9,816,099 B2
(45) Date of Patent: Nov. 14, 2017

(54) GENE FOR INCREASING PLANT WEIGHT AND METHOD FOR USING THE SAME

(71) Applicant: TOYOTA JIDOSHA KABUSHIKI KAISHA, Toyota-shi, Aichi (JP)

(72) Inventors: Satoshi Kondo, Miyoshi (JP); Chikara Ohto, Toyota (JP); Masaru Takagi, Tsuchiura (JP); Kyoko Matsui, Ryugasaki (JP); Tomotsugu Koyama, Tsukuba (JP); Nobutaka Mitsuda, Tsukuba (JP); Nobuhiko Muramoto, Ichinomiya (JP); Norihiro Mitsukawa, Miyoshi (JP); Tomoko Tanaka, Nogoya (JP)

(73) Assignee: TOYOTA JIDOSHA KABUSHIKI KAISHA, Toyota-shi, Aichi (JP)

( * ) Notice: Subject to any disclaimer, the term of this patent is extended or adjusted under 35 U.S.C. 154(b) by 0 days.

(21) Appl. No.: 15/045,924

(22) Filed: Feb. 17, 2016

(65) Prior Publication Data

US 2016/0160227 A1   Jun. 9, 2016

Related U.S. Application Data

(62) Division of application No. 13/376,138, filed as application No. PCT/JP2010/003761 on Jun. 4, 2010, now Pat. No. 9,303,265.

(30) Foreign Application Priority Data

Jun. 4, 2009 (JP) ................................. 2009-135309

(51) Int. Cl.
   C12N 15/82 (2006.01)
   C07K 14/415 (2006.01)

(52) U.S. Cl.
   CPC ........ *C12N 15/8247* (2013.01); *C07K 14/415* (2013.01); *C12N 15/82* (2013.01); *C12N 15/8261* (2013.01)

(58) Field of Classification Search
   CPC .............................................. C12N 15/8247
   See application file for complete search history.

(56) References Cited

U.S. PATENT DOCUMENTS

| | | | |
|---|---|---|---|
| 5,516,668 A | 5/1996 | Maruta | |
| 5,783,394 A | 7/1998 | Bestwick et al. | |
| 5,914,449 A | 6/1999 | Murase et al. | |
| 6,717,034 B2 | 4/2004 | Jiang | |
| 7,342,148 B2 | 3/2008 | Takagi et al. | |
| 2003/0101481 A1 | 5/2003 | Zhang et al. | |
| 2003/0226173 A1 | 12/2003 | Ratcliffe et al. | |
| 2004/0006797 A1 | 1/2004 | Shi et al. | |
| 2004/0045049 A1 | 3/2004 | Zhang et al. | |
| 2004/0093638 A1 | 5/2004 | Sasaki et al. | |
| 2005/0005333 A1 | 1/2005 | Ruezinsky et al. | |
| 2005/0183169 A1 | 8/2005 | Takagi et al. | |
| 2006/0107345 A1 | 5/2006 | Alexandrov et al. | |
| 2006/0272060 A1 | 11/2006 | Heard et al. | |
| 2007/0022495 A1 | 1/2007 | Reuber et al. | |
| 2008/0072340 A1 | 3/2008 | Troukhan et al. | |
| 2008/0096277 A1 | 4/2008 | Kuroda | |
| 2009/0019605 A1 | 1/2009 | Takagi et al. | |
| 2009/0094717 A1 | 4/2009 | Troukhan et al. | |
| 2009/0116723 A1 | 5/2009 | Okajima et al. | |
| 2009/0178161 A1 | 7/2009 | Arar et al. | |
| 2009/0190821 A1 | 7/2009 | Marugame | |
| 2009/0300790 A1 | 12/2009 | Aharoni et al. | |
| 2010/0311994 A1 | 12/2010 | Chatani et al. | |
| 2011/0010804 A1 | 1/2011 | Chatani et al. | |
| 2011/0081691 A1 | 4/2011 | Ohto et al. | |
| 2011/0099664 A1 | 4/2011 | Takagi et al. | |
| 2011/0209244 A1 | 8/2011 | Takagi et al. | |
| 2012/0144522 A1 | 6/2012 | Kondo et al. | |
| 2012/0159666 A1 | 6/2012 | Yonekura et al. | |

FOREIGN PATENT DOCUMENTS

| | | |
|---|---|---|
| EP | 1 469 010 A1 | 10/2004 |
| EP | 1 586 652 A1 | 10/2005 |
| EP | 1702508 A1 | 9/2006 |
| JP | 60-2023 B2 | 1/1985 |
| JP | 2-035358 A | 2/1990 |
| JP | 06-090766 A | 4/1994 |
| JP | 6-217719 A | 8/1994 |
| JP | 6-303925 A | 11/1994 |
| JP | 9-182 A | 1/1997 |
| JP | 9-65840 A | 3/1997 |
| JP | 09-313059 A | 12/1997 |
| JP | 2001-059842 A | 3/2001 |
| JP | 3149951 B2 | 3/2001 |

(Continued)

OTHER PUBLICATIONS

Nature 408 (6814), 820-822 (2000).*
Nature 408 (6814): pp. 820-822 (2000).*
Akane Matsushita, et al., "AGF1, an AT-Hook Protein, Is Necessary for the Negative Feedback of AtGA3ox1 Encoding GA 3-Oxidase1[w]", Plant Physiology, Mar. 2007, pp. 1152-1162, vol. 143.
Alex Cernac, et al., "WRINKLED1 encodes an AP2/EREB domain protein involved in the control of storage compound biosynthesis in Arabidopsis", The Plant Journal, 2004, pp. 575-585, vol. 40.
Antony N. Dodd., et al., "Plant Circadian Clocks Increase Photosynthesis, Growth, Survival, and Competitive Advantage", Science, Jul. 22, 2005, pp. 630-633, vol. 309.
Colette Jako, et al., "Seed-Specific Over-Expression of an Arabidopsis cDNA Encoding a Diacylglycerol Acyltransferase Enhances Seed Oil Content and Seed Weight", Plant Physiology, Jun. 2001, pp. 861-874, vol. 126.
Diego Mauricio Riano-Pachon, et al., "Pln TFDB an integrative plant transcription factor database", BMC Bioinformatics, 2007, pp. 1-10, vol. 8. No. 42.

(Continued)

*Primary Examiner* — Russell Kallis
(74) *Attorney, Agent, or Firm* — Sughrue Mion, PLLC

(57) ABSTRACT

A gene having novel functions is searched for, by which plant weight (that is, biomass level) can be increased and by which substance productivity can be increased or decreased. A chimeric protein is expressed in which a transcriptional factor comprising the amino acid sequence shown in SEQ ID NO: 2, 4, or 6 is fused to a functional peptide that converts an arbitrary transcriptional factor into a transcriptional repression factor.

10 Claims, No Drawings

(56) References Cited

FOREIGN PATENT DOCUMENTS

| | | |
|---|---|---|
| JP | 2001-269176 A | 10/2001 |
| JP | 2001-269177 A | 10/2001 |
| JP | 2001-269178 A | 10/2001 |
| JP | 2001-269179 A | 10/2001 |
| JP | 2001-292776 A | 10/2001 |
| JP | 2001-292777 A | 10/2001 |
| JP | 3407034 B2 | 10/2001 |
| JP | 2001-333705 A | 12/2001 |
| JP | 3289043 B2 | 3/2002 |
| JP | 2002-524028 A | 8/2002 |
| JP | 3407033 B2 | 3/2003 |
| JP | 3407035 B2 | 3/2003 |
| JP | 3409079 B2 | 3/2003 |
| JP | 3421740 B2 | 4/2003 |
| JP | 3407036 B2 | 5/2003 |
| JP | 2004-500823 A | 1/2004 |
| JP | 2004-286666 A | 10/2004 |
| JP | 2005-013214 A | 1/2005 |
| JP | 2005-027654 A | 2/2005 |
| JP | 2005-052114 A | 3/2005 |
| JP | 3656104 B2 | 3/2005 |
| JP | 2005-192483 A | 7/2005 |
| JP | 2005-204573 A | 8/2005 |
| JP | 2005-204657 A | 10/2005 |
| JP | 2005-278422 A | 10/2005 |
| JP | 2005-295878 A | 10/2005 |
| JP | 2005-295879 A | 10/2005 |
| JP | 2005-325136 A | 11/2005 |
| JP | 2005-352571 A | 12/2005 |
| JP | 2006-006248 A | 1/2006 |
| JP | 2006-020607 A | 1/2006 |
| JP | 2006-034218 A | 2/2006 |
| JP | 2006-042729 A | 2/2006 |
| JP | 2006-042730 A | 2/2006 |
| JP | 2006-055125 A | 3/2006 |
| JP | 2006-101827 A | 4/2006 |
| JP | 2006-134188 A | 5/2006 |
| JP | 2006-280242 A | 10/2006 |
| JP | 3829200 B2 | 10/2006 |
| JP | 2006-325588 A | 12/2006 |
| JP | 3995211 B2 | 10/2007 |
| JP | 2008-502358 A | 1/2008 |
| JP | 2009-009290 A | 1/2009 |
| JP | 2009-115598 A | 5/2009 |
| JP | 2009-180539 A | 8/2009 |
| JP | 2009-210409 A | 9/2009 |
| WO | 00/05385 A1 | 2/2000 |
| WO | 01/35727 A1 | 5/2001 |
| WO | 01/36597 A1 | 5/2001 |
| WO | 01/64022 A2 | 9/2001 |
| WO | 03/013227 A2 | 2/2003 |
| WO | 03/055903 A1 | 7/2003 |
| WO | 2004031349 A2 | 4/2004 |
| WO | 2004/046336 A2 | 6/2004 |
| WO | 2004/056993 A1 | 7/2004 |
| WO | 2005047516 A2 | 5/2005 |
| WO | 2005/085467 A1 | 9/2005 |
| WO | 2006/056701 A1 | 6/2006 |
| WO | 2006133461 A1 | 12/2006 |
| WO | 2007/078280 A2 | 7/2007 |
| WO | 2007/102346 A1 | 9/2007 |
| WO | 2007/117693 A2 | 10/2007 |
| WO | 2008/041693 A1 | 4/2008 |
| WO | 2010/035618 A1 | 4/2010 |
| WO | 2010/041423 A1 | 4/2010 |

OTHER PUBLICATIONS

Jisheng Li, et al., "Arabidopsis H+ -PPase AVP1 Regulates Auxin-Mediated Organ Development", Science, Oct. 7, 2005, pp. 121-125, vol. 310.

Keiichiro Hiratsu, et al., "Dominant repression of target genes by chimeric repressors that include the EAR motif, a repression domain, in Arabidopsis", The Plant Journal, 2003, pp. 733-739, vol. 34.

Kyoko Matsui, et al., "AtMYBL2, a protein with a single MYB domain, acts as a negative regulator of anthocyanin biosynthesis in Arabidopsis", The Plant Journal, 2008, pp. 954-967, vol. 55.

Marie C. Schruff, et al., "The Auxin Response Factor 2 gene of Arabidopsis links auxin signaling, cell division, and the size of seeds and other organs", Development, Nov. 1, 2005, pp. 251-261, vol. 133.

Minoru Kubo, et al., "Transcription switches for protoxylem and metaxylem vessel formation", Genes & Development, 2005, pp. 1855-1860, vol. 19.

Nobutaka Mitsuda, et al., "NAC Transcription Factors, NST1 and NST3, Are Key Regulators of the Formation of Secondary Walls in Woody Tissues of Arabidopsis", The Plant Cell, Jan. 2007, pp. 270-280, vol. 19.

Norihito Kuno, et al., "The Novel MYB Protein Early-Phytochrome-RESPONSIVE1 Is a Component of a Slave Circadian Oscillator in Arabidopsis", The Plant Cell, Oct. 2003, pp. 2476-2488, vol. 15.

Office Action issued in U.S. Appl. No. 12/746,577, dated Oct. 23, 2013.

Office Action issued in U.S. Appl. No. 12/921,060, dated Oct. 8, 2013.

Summaries of a Conference of Japan Society for Bioscience, Biotechnology, and Agrochemistry, 2008, vol. 2008, p. 64.

Yongfeng Guo, et al., "AtNAP, a NAC family transcription factor, has an important role in leaf senescence", The Plant Journal, 2006, pp. 601-612, vol. 46.

Yukiko Mizukami, et al., "Plant organ size control: AINTEGUMENTA regulates growth and cell numbers during organogenesis", PNAS, Jan. 18, 2000, pp. 942-947, vol. 97, No. 2.

Yuxin Hu, et al., "The Arabidopsis Auxin-Inducible Gene ARGOS Controls Lateral Organ Size", The Plant Cell, Sep. 2003, pp. 1951-1961, vol. 15.

Yuxin Hu., et al., "The Arabidopsis ARGOS-LIKE gene regulates cell expansion during organ growth", The Plant Journal, 2006, pp. 1-9, vol. 47.

Zhongfu Ni, et al., "Altered circadian rhythms regulate growth vigour in hybrids and allopolyploids", Nature, Jan. 15, 2009, pp. 327-331, vol. 457.

Notice of Allowance, dated Feb. 11, 2015, issued by the United States Patent and Trademark Office in U.S. Appl. No. 12/921,060.

Guo et al., "Protein Tolerance to Random Amino Acid Change," 2004, pp. 9205-9210, PNAS, vol. 101, No. 25.

Kunieda et al., "NAC Family Proteins NARS1/NAC2 and NARS2/NAM in the Outer Integument Regulate Embryogenesis in Arabidopsis," Oct. 2008, pp. 2631-2642, The Plant Cell, vol. 20.

Takeda et al., "RNA Interference of the Arabidopsis Putative Transcription Factor TCP16 Gene Results in Abortion of Early Pollen Development," 2006, pp. 165-177, Plant Molecular Biology, vol. 61.

Kuno et al., "The Novel MYB Protein EARLY-PHYTOCHROM-RESPONSIVE1 is a Component of a Slave Circadian Oscillator in Arabidopsis," Oct. 2003, pp. 2476-2488, vol. 15.

Extended European Search Report (EESR) for corresponding European Patent Application No. 08 85 6425.7, dated Nov. 3, 2010.

Mingjie Chen et al., "System Analysis of an Arabidopsis Mutant Altered in de Novo Fatty Acid Synthesis Reveals Diverse Changes in Seed Composition and Metabolism", Plant Physiology, 2009, 150: 27-41.

John Doebley et al., "The evolution of apical dominance in maize", Nature, 1997, 386: 485-488.

International Search Report for International Application No. PCT/JP2010/059543, dated Aug. 17, 2010.

Tomotsugu Koyama et al., "TCP Transcription Factors Control the Morphology of Shoot Lateral Organs via Negative Regulation of the Expression of Boundary-Specific Genes in Arabidopsis", The Plant Cell, 2007, 19: 473-484.

Makoto Kusaba et al., "Low glutelin content1: A Dominant Mutation that Suppresses the Glutelin Multigene Family via RNA Silencing in Rice", The Plant Cell, 2003, 15: 1455-1467.

(56) References Cited

OTHER PUBLICATIONS

Hon-Ming Lam, et al., "Overexpression of the ASN1 Gene Enhances Nitrogen Status in Seeds of Arabidopsis", Plant Physiology, 2003, 132:926-935.
Yoshiyuki Maruta et al., "Transgenic rice with reduced glutelin content by transformation with glutelin A antisense gene", Molecular Breeding, 2001, 8:273-284.
Nobuhiko Muramoto et al., "Identification of transcription factors responsible for seed oil content by Chimeric Repressor Gene-Silencing Technology (CRES-T)", Supplemental to Plant and Cell Physiology, 2008, 49:152.
Akio Ohyama et al., "Environmental risk evaluation of rice plants transformed with chimeric antisense cDNA for glutelin", Breeding Research, 2001, 3: 139-149.
Keith Roesler, et al., "Targeting of the Arabidopsis Homomeric Acetyl-Coenzyme A Carboxylase to Plastids of Rapeseeds", Plant Physiology, 1997, pp. 75-81, vol. 113, Clearance Center.
Monica Santos-Mendoza et al., "Deciphering gene regulatory networks that control seed development and maturation in Arabidopsis", The Plant Journal, 2008, 54: 608-620.
Taito Takeda et al., "RNA interference of the Arabidopsis putative transcription factor TCP16 gene results in abortion of early pollen development", Plant Molecular Biology, 2006, 61: 165-177.
Kyoko Matsui, et al., "Suppression of the biosynthesis of proanthocyanidin in Arabidopsis by a chimeric PAP1 repressor", Plant Biotechnology Journal, 2004, pp. 487-493, vol. 2, Blackwell Publishing Ltd.
Keiichiro Hiratsu, et al., "Identification of the minimal repression domain of SUPERMAN shows that the DLELRL hexapeptide is both necessary and sufficient for repression of transcription in Arabidopsis", Biochemical and Biophysical Research Communications, 2004, pp. 172-178, vol. 321, Elsevier Inc.
Keiichiro Hiratsu, et al., "The SUPERMAN protein is an active repressor whose carboxy-terminal repression domain is required for the development of normal flowers", Federation of European Biochemical Societies, 2002, pp. 351-354, vol. 514, Elsevier Science B.V.
Kyoko Matsui, et al., "Bio Medical Quick Review Net", 2004, pp. 1-6, vol. 4006.
Kyoko Matsui, "A Chimeric AtMYB23 Repressor Induces Hairy Roots, Elongation of Leaves and Stems, and Inhibition of the Deposition of Mucilage on Seed Coats in Arabidopsis", Plant Cell Physiology, 2005, pp. 147-155, vol. 46(1).
Daniel Zilberman, et al., "ARGONAUTE4 Control of Locus-Specific siRNA Accumulation and DNA and Histone Methylation", Science, Jan. 2003, pp. 716-719, vol. 299, American Association for the Advancement of Science.
James P. Jackson, et al., "Control of CpNpG DNA methylation by the KRYPTONITE histone H3 methyltransferase", Letters to Nature, Apr. 2002, pp. 556-560, vol. 416, Macmillan Magazines Ltd.
Xiaofeng Cao, et al., "Role of the Arabidopsis DRM Methyltransferases in De Novo DNA Methylation and Gene Silencing", Current Biology, Jul. 2002, pp. 1138-1144, vol. 12, Elsevier Science Ltd.
Xiaofeng Cao, et al., "Locus-specific control of asymmetric and CpNpG methylation by the DRM and CMT3 methyltransferase genes", PNAS, Dec. 2002, pp. 16491-16498, vol. 99, Suppl. 4.
Lu Tian et al., "Blocking histone deacetylation in Arabidopsis induces pleiotropic effects on plant gene regulation and development", PNAS, Jan. 2001, pp. 200-205, vol. 98, No. 1.
Anders M. Lindroth, et al., "Requirement of CHROMOMETHYLASE3 for Maintenance of CpXpG Methylation", Science, Jun. 2001, pp. 2077-2080, vol. 292, American Association for the Advancement of Science, Washington, DC.
Steven E. Jacobsen, et al., "Hypermethylated SUPERMAN Epigenetic Alleles in Arabidopsis", Science, Aug. 1997, pp. 1100-1103, vol. 277, American Association for the Advancement of Science, Washington, DC.
Steven E. Jacobsen, et al., "Ectopic hypermethylation of flower-specific genes in Arabidopsis", Current Biology, 2000, pp. 179-186, vol. 10, No. 4, Elsevier Science Ltd.
John L. Bowman, et al., "SUPERMAN, a regulator of floral homeotic genes in Arabidopsis", Development, 1992, pp. 599-615, vol. 114, The Company of Biologists Limited, Great Britain.
J. Christopher Gaiser, et al., "The Arabidopsis SUPERMAN Gene Mediates Asymmetric Growth of the Outer Integument of Ovules", The Plant Cell, Mar. 1995, pp. 333-345, vol. 7, American Society of Plant Physiologists.
Koji Goto, et al., "Function and regulation of the Arabidopsis floral homeotic gene PISTILLATA", Genes & Development, 1994, pp. 1548-1560, vol. 8, Cold Spring Harbor Laboratory Press.
Masaru Ohta, et al., "Repression Domains of Class II ERF Transcriptional Repressors Share and Essential Motif for Active Repression", The Plant Cell, Aug. 2001, pp. 1959-1968, vol. 13, American Society of Plant Biologists.
N. Mitsuda et al., Abstracts of the 45th Annual Meeting of the Japanese Society of Plant Physiologists (2004) P4-B-16 (813).
S. Takada et al., Accession No. AB049071, The CUP-SHAPED COYTLEDON1 gene of Arabidopsis regulates shoot apical meristem formation, Database NCBI/GenBank (online), 2006, retrieved from . http://www.ncbi.nlm.nih.gov/entrez/viewer.fcgi712060425:DDBJ:5636984 on Dec. 25, 2008.
K. Yamada et al., Accession No. BT005044, Arabidopsis Open Reading Frame (ORF) Clones, Database NCBI/GenBank (online), 2003, retrieved from . httD://www.ncbi.nlm.nih.jTOv/entrez/viewer.fcgi?28827465:NCBI:4515668 on Dec. 25, 2008.
Toshitsugu Nakano et al., "Genome-Wide Analysis of the ERF Gene Family in Arabidopsis and Rice", Plant Physiology, 2006, 140: 411-432.
Y. Pan et al., "Molecular Cloning, Expression, Phylogenetic and Functional Characterization of the Arabidopsis AP2/EREBP Transcription Factor Family", GenBank Accession AY560877, 2004 retrieved from: http://www.ncbi.nlm.nih.gov/entrez/viewer.fcgi?48479345:NCBI:6713742 on Dec. 25, 2008.
V.R. Bautista et al., "Arabidopsis ORF clones", GenBank Accession BT029518, 2006, retrieved from: http://www.ncbi.nlm.nih.gov/entrez/viewer.fcgi?119360090:NCBI:15965543 on Dec. 25, 2008.
Shinchiro Sawa, "Overexpression of the AtmybL2 Gene Represses Trichome Development in Arabidopsis", DNA Research, 2002, pp. 31-34, vol. 9, No. 2.
Bo Shen et al., "The homeobox gene GLABRA2 affects seed oil content in Arabidopsis", Plant Molecular Biology, 2006, 60: 377-387.
Christian Dubos et al., "MYB transcription factors in Arabidopsis", Trends in Plant Science, 2010, 15(10): 573-581.
Haiwei H. Guo et al., "Protein tolerance to random amino acid change", PNAS, 2004, 101(25): 9205-9210.
"Represent" from Merriam-Webster Dictionary, Retrieved from http://www.merriam-webster.com/dictionary/represents on Feb. 5, 2013.
Ralf Stracke et al., "The R2R3-MYB gene family in *Arabidopsis thaliana*", Current Opinion in Plant Biology, 2001, 4: 447-456.
Geoffrey M. Wahl et al., "Molecular Hybridization of Immobilized Nucleic Acids: Theoretical Concepts and Practical Considerations", Methods in Enzymology, 1987, 152: 399-407.
Randall J. Weselake et al., "Increasing the flow of carbon into seed oil", Biotechnology Advances, 2009, 27: 866-878.
Joseph A. White et al., "Genomic approaches towards the engineering of oil seeds", Plant Physiology and Biochemistry, 2001, 39: 263-270.
Chen Yanhui et al., "The MYB transcription factor superfamily of Arabidopsis: expression analysis and phylogenetic comparison with the rice MYB family", Plant Molecular Biology, 2006, 60(1): 107-124.
James Z. Zhang, "Overexpression Analysis of Plant Transcription Factors", Current Opinion in Plant Biology, 2003, 6: 430-440.
Gaiyun Zhang et al., Phylogeny, gene structures, and expression patterns of the ERF gene family in soybean (Glycine max L.), Journal of Experimental Botany, 2008, 59(15): 4095-4107.
Ohto, 22nd International Conference on Arabidopsis Research, 2011, Pub: 501746623.

(56) References Cited

OTHER PUBLICATIONS

K. Diane Jofuku et al., "Control of seed mass and seed yield by the floral homeotic gene APETALA2", PNAS, 2005, 102(8): 3117-3122.
International Search Report for International Application No. PCT/JP2008/072158, dated Feb. 24, 2009.
Extended European Search Report (EESR) for corresponding European Patent Application No. 08858128.5, dated Nov. 15, 2010.
Restriction/Election of Species Requirement issued in U.S. Appl. No. 12/746,577, mailed on Aug. 16, 2013.
Non-Final Office Action issued in U.S. Appl. No. 12/746,577, mailed on Feb. 15, 2013.
Notice to Comply issued in U.S. Appl. No. 12/746,640, mailed on Aug. 16, 2012.
Non-Final Office Action issued in U.S. Appl. No. 12/746,640, mailed on Nov. 27, 2012.
Non-Final Office Action issued in U.S. Appl. No. 12/921,060, mailed on Feb. 19, 2013.
Final Office Action issued in U.S. Appl. No. 12/746,640, mailed on Jul. 2, 2013.
Non Final Office Action, dated Feb. 11, 2015, issued by the U.S. Patent and Trademark Office in U.S. Appl. No. 13/376,138.
Final Office Action, dated Jul. 27, 2015, issued by the U.S. Patent and Trademark Office in U.S. Appl. No. 13/376,138.
Notice of Allowance, dated Nov. 19, 2015, issued by the U.S. Patent and Trademark Office in U.S. Appl. No. 13/376,138.
Notice of Allowance and Issue Fee(s) Due for U.S. Appl. No. 15/045,853 dated May 17, 2017.
Notice of Allowance, dated Sep. 13, 2017, issued by The United States Patent and Trademark Office in U.S. Appl. No. 15/045,853.

* cited by examiner

SEQUENCE LISTING

```
<160> NUMBER OF SEQ ID NOS: 21

<210> SEQ ID NO 1
<211> LENGTH: 1080
<212> TYPE: DNA
<213> ORGANISM: Arabidopsis thaliana
<220> FEATURE:
<221> NAME/KEY: CDS
<222> LOCATION: (1)..(1080)

<400> SEQUENCE: 1 atg ata agc aag gat cca aga tcg agt tta cct cca ggg ttt cga ttt      48
Met Ile Ser Lys Asp Pro Arg Ser Ser Leu Pro Pro Gly Phe Arg Phe
1               5                   10                  15 cat cca aca gat gaa gaa ctc att ctc cat tac cta agg aag aaa gtt      96
```

```
                His Pro Thr Asp Glu Glu Leu Ile Leu His Tyr Leu Arg Lys Lys Val
                             20                  25                  30 tcc tct tcc cca gtc ccg ctt tcg att atc gcc gat gtc gat atc tac         144
Ser Ser Ser Pro Val Pro Leu Ser Ile Ile Ala Asp Val Asp Ile Tyr
                35                  40                  45 aaa tcc gat cca tgg gat tta cca gct aag gct cca ttt ggg gag aaa         192
Lys Ser Asp Pro Trp Asp Leu Pro Ala Lys Ala Pro Phe Gly Glu Lys
        50                  55                  60 gag tgg tat ttt ttc agt ccg agg gat agg aaa tat cca aac gga gca         240
Glu Trp Tyr Phe Phe Ser Pro Arg Asp Arg Lys Tyr Pro Asn Gly Ala
65                  70                  75                  80 aga cca aac aga gca gct gcg tct gga tat tgg aaa gca acc gga aca         288
Arg Pro Asn Arg Ala Ala Ala Ser Gly Tyr Trp Lys Ala Thr Gly Thr
                85                  90                  95 gat aaa ttg att gcg gta cca aat ggt gaa ggg ttt cat gaa aac att         336
Asp Lys Leu Ile Ala Val Pro Asn Gly Glu Gly Phe His Glu Asn Ile
                100                 105                 110 ggt ata aaa aaa gct ctt gtg ttt tat aga gga aag cct cca aaa ggt         384
Gly Ile Lys Lys Ala Leu Val Phe Tyr Arg Gly Lys Pro Pro Lys Gly
        115                 120                 125 gtt aaa acc aat tgg atc atg cat gaa tat cgt ctt gcc gat tca tta         432
Val Lys Thr Asn Trp Ile Met His Glu Tyr Arg Leu Ala Asp Ser Leu
130                 135                 140 tct ccc aaa aga att aac tct tct agg agc ggt ggt agc gaa gtt aat         480
Ser Pro Lys Arg Ile Asn Ser Ser Arg Ser Gly Gly Ser Glu Val Asn
145                 150                 155                 160 aat aat ttt gga gat agg aat tct aaa gaa tat tcg atg aga ctg gat         528
Asn Asn Phe Gly Asp Arg Asn Ser Lys Glu Tyr Ser Met Arg Leu Asp
                165                 170                 175 gat tgg gtt ctt tgc cgg att tac aag aaa tca cac gct tca ttg tca         576
Asp Trp Val Leu Cys Arg Ile Tyr Lys Lys Ser His Ala Ser Leu Ser
        180                 185                 190 tca cct gat gtt gct ttg gtc aca agc aat caa gag cat gag gaa aat         624
Ser Pro Asp Val Ala Leu Val Thr Ser Asn Gln Glu His Glu Glu Asn
        195                 200                 205 gac aac gaa cca ttc gta gac cgc gga acc ttt ttg cca aat ttg caa         672
Asp Asn Glu Pro Phe Val Asp Arg Gly Thr Phe Leu Pro Asn Leu Gln
210                 215                 220 aat gat caa ccc ctt aaa cgc cag aag tct tct tgt tcg ttc tca aac         720
Asn Asp Gln Pro Leu Lys Arg Gln Lys Ser Ser Cys Ser Phe Ser Asn
225                 230                 235                 240 tta cta gac gct aca gat ttg acg ttt ctc gca aat ttt cta aac gaa         768
Leu Leu Asp Ala Thr Asp Leu Thr Phe Leu Ala Asn Phe Leu Asn Glu
                245                 250                 255 acc ccg gaa aat cgt tct gaa tca gat ttt tct ttc atg att ggc aat         816
Thr Pro Glu Asn Arg Ser Glu Ser Asp Phe Ser Phe Met Ile Gly Asn
        260                 265                 270 ttc tct aat cct gac att tac gga aac cat tac ttg gat cag aag tta         864
Phe Ser Asn Pro Asp Ile Tyr Gly Asn His Tyr Leu Asp Gln Lys Leu
        275                 280                 285 ccg cag ttg agc tct ccc act tca gag aca agc ggc atc gga agc aaa         912
Pro Gln Leu Ser Ser Pro Thr Ser Glu Thr Ser Gly Ile Gly Ser Lys
        290                 295                 300 aga gag aga gtg gat ttt gcg gaa gaa acg ata aac gct tcg aag aag         960
Arg Glu Arg Val Asp Phe Ala Glu Glu Thr Ile Asn Ala Ser Lys Lys
305                 310                 315                 320 atg atg aac aca tat agt tac aat aat agt ata gat caa atg gat cat        1008
Met Met Asn Thr Tyr Ser Tyr Asn Asn Ser Ile Asp Gln Met Asp His
                325                 330                 335
```

```
agt atg atg caa caa cct agt ttc ctg aac cag gaa ctc atg atg agt    1056
Ser Met Met Gln Gln Pro Ser Phe Leu Asn Gln Glu Leu Met Met Ser
        340                 345                 350 tct cac ctt caa tat caa ggc tag                                    1080
Ser His Leu Gln Tyr Gln Gly
        355
```

<210> SEQ ID NO 2
<211> LENGTH: 359
<212> TYPE: PRT
<213> ORGANISM: Arabidopsis thaliana

<400> SEQUENCE: 2

```
Met Ile Ser Lys Asp Pro Arg Ser Ser Leu Pro Pro Gly Phe Arg Phe
1               5                   10                  15

His Pro Thr Asp Glu Glu Leu Ile Leu His Tyr Leu Arg Lys Lys Val
            20                  25                  30

Ser Ser Ser Pro Val Pro Leu Ser Ile Ile Ala Asp Val Asp Ile Tyr
        35                  40                  45

Lys Ser Asp Pro Trp Asp Leu Pro Ala Lys Ala Pro Phe Gly Glu Lys
    50                  55                  60

Glu Trp Tyr Phe Phe Ser Pro Arg Asp Arg Lys Tyr Pro Asn Gly Ala
65                  70                  75                  80

Arg Pro Asn Arg Ala Ala Ala Ser Gly Tyr Trp Lys Ala Thr Gly Thr
                85                  90                  95

Asp Lys Leu Ile Ala Val Pro Asn Gly Glu Gly Phe His Glu Asn Ile
            100                 105                 110

Gly Ile Lys Lys Ala Leu Val Phe Tyr Arg Gly Lys Pro Pro Lys Gly
        115                 120                 125

Val Lys Thr Asn Trp Ile Met His Glu Tyr Arg Leu Ala Asp Ser Leu
    130                 135                 140

Ser Pro Lys Arg Ile Asn Ser Arg Ser Gly Gly Ser Glu Val Asn
145                 150                 155                 160

Asn Asn Phe Gly Asp Arg Asn Ser Lys Glu Tyr Ser Met Arg Leu Asp
                165                 170                 175

Asp Trp Val Leu Cys Arg Ile Tyr Lys Lys Ser His Ala Ser Leu Ser
            180                 185                 190

Ser Pro Asp Val Ala Leu Val Thr Ser Asn Gln Glu His Glu Glu Asn
        195                 200                 205

Asp Asn Glu Pro Phe Val Asp Arg Gly Thr Phe Leu Pro Asn Leu Gln
    210                 215                 220

Asn Asp Gln Pro Leu Lys Arg Gln Lys Ser Ser Cys Ser Phe Ser Asn
225                 230                 235                 240

Leu Leu Asp Ala Thr Asp Leu Thr Phe Leu Ala Asn Phe Leu Asn Glu
                245                 250                 255

Thr Pro Glu Asn Arg Ser Glu Ser Asp Phe Ser Phe Met Ile Gly Asn
            260                 265                 270

Phe Ser Asn Pro Asp Ile Tyr Gly Asn His Tyr Leu Asp Gln Lys Leu
        275                 280                 285

Pro Gln Leu Ser Ser Pro Thr Ser Glu Thr Ser Gly Ile Gly Ser Lys
    290                 295                 300

Arg Glu Arg Val Asp Phe Ala Glu Glu Thr Ile Asn Ala Ser Lys Lys
305                 310                 315                 320

Met Met Asn Thr Tyr Ser Tyr Asn Asn Ser Ile Asp Gln Met Asp His
                325                 330                 335
```

```
Ser Met Met Gln Gln Pro Ser Phe Leu Asn Gln Glu Leu Met Met Ser
            340                 345                 350

Ser His Leu Gln Tyr Gln Gly
        355

<210> SEQ ID NO 3
<211> LENGTH: 1119
<212> TYPE: DNA
<213> ORGANISM: Arabidopsis thaliana
<220> FEATURE:
<221> NAME/KEY: CDS
<222> LOCATION: (1)..(1119)

<400> SEQUENCE: 3 atg ctc tgt ttt gtt cgc ttt cag gct ggt ttt gtg aga att ata gtt      48
Met Leu Cys Phe Val Arg Phe Gln Ala Gly Phe Val Arg Ile Ile Val
1               5                   10                  15 gca gca aga aag cgt ttc aga tat ttt tta atg gcc gct gag gat cga      96
Ala Ala Arg Lys Arg Phe Arg Tyr Phe Leu Met Ala Ala Glu Asp Arg
                20                  25                  30 agt gag gaa cta agc agc aat gta gaa aat gga agt tgc aat tcc aat     144
Ser Glu Glu Leu Ser Ser Asn Val Glu Asn Gly Ser Cys Asn Ser Asn
            35                  40                  45 gaa gga att aat cct gaa acc agc agt cat tgg att gaa aac gtt gtc     192
Glu Gly Ile Asn Pro Glu Thr Ser Ser His Trp Ile Glu Asn Val Val
        50                  55                  60 aag gtt agg aaa ccg tac aca gta act aag cag aga gag aag tgg agt     240
Lys Val Arg Lys Pro Tyr Thr Val Thr Lys Gln Arg Glu Lys Trp Ser
65                  70                  75                  80 gag gaa gag cat gat agg ttt ctt gaa gct atc aag ctt tat ggt cgt     288
Glu Glu Glu His Asp Arg Phe Leu Glu Ala Ile Lys Leu Tyr Gly Arg
                85                  90                  95 ggt tgg cgt caa atc caa gaa cac ata ggt aca aaa acc gct gta cag     336
Gly Trp Arg Gln Ile Gln Glu His Ile Gly Thr Lys Thr Ala Val Gln
                100                 105                 110 ata cga agc cat gct caa aag ttc ttc tcc aag atg gct cag gaa gct     384
Ile Arg Ser His Ala Gln Lys Phe Phe Ser Lys Met Ala Gln Glu Ala
            115                 120                 125 gac agt aga agt gaa gga tcg gtt aaa gcg att gtg atc ccg cct cct     432
Asp Ser Arg Ser Glu Gly Ser Val Lys Ala Ile Val Ile Pro Pro Pro
        130                 135                 140 cgt cca aag aga aaa ccg gca cat cct tat cct cgg aaa tcg cct gtt     480
Arg Pro Lys Arg Lys Pro Ala His Pro Tyr Pro Arg Lys Ser Pro Val
145                 150                 155                 160 cca tat act cag tct cct cca cca aat ttg tca gct atg gag aaa gga     528
Pro Tyr Thr Gln Ser Pro Pro Pro Asn Leu Ser Ala Met Glu Lys Gly
                165                 170                 175 acc aag tct cca acc tca gtg tta tca tcg ttt ggt tca gag gat caa     576
Thr Lys Ser Pro Thr Ser Val Leu Ser Ser Phe Gly Ser Glu Asp Gln
            180                 185                 190 gtc aat aga tgc tct tcg cct aat tcg tgt acc agt gac atc caa tcc     624
Val Asn Arg Cys Ser Ser Pro Asn Ser Cys Thr Ser Asp Ile Gln Ser
        195                 200                 205 att ggt gca act tcc att gat aaa aag aat aac tac aca aca tcc aag     672
Ile Gly Ala Thr Ser Ile Asp Lys Lys Asn Asn Tyr Thr Thr Ser Lys
    210                 215                 220 caa cct ttc aaa gat gat tct gac att ggt tca aca ccc att tca agc     720
Gln Pro Phe Lys Asp Asp Ser Asp Ile Gly Ser Thr Pro Ile Ser Ser
225                 230                 235                 240 att act ctt ttc ggg aag att gtc ctt gtc gcg gaa gaa tct cac aaa     768
Ile Thr Leu Phe Gly Lys Ile Val Leu Val Ala Glu Glu Ser His Lys
```

-continued

```
                  245                 250                 255
cca tcc tct tac aat gat gat gat ctt aaa caa atg acg tgt cag gag       816
Pro Ser Ser Tyr Asn Asp Asp Asp Leu Lys Gln Met Thr Cys Gln Glu
        260                 265                 270 aat cac tac tca ggg atg cta gtt gac act aat tta tct ctt ggt gta       864
Asn His Tyr Ser Gly Met Leu Val Asp Thr Asn Leu Ser Leu Gly Val
            275                 280                 285 tgg gaa acg ttt tgt act ggt tct aat gca ttt ggc tcg gtt aca gaa       912
Trp Glu Thr Phe Cys Thr Gly Ser Asn Ala Phe Gly Ser Val Thr Glu
290                 295                 300 gca tct gag aac ttg gag aaa agt gca gag ccg ata agt tct tca tgg       960
Ala Ser Glu Asn Leu Glu Lys Ser Ala Glu Pro Ile Ser Ser Ser Trp
305                 310                 315                 320 aaa cgg tta agc tcc tta gaa aaa caa gga tct tgt aat cct gta aat      1008
Lys Arg Leu Ser Ser Leu Glu Lys Gln Gly Ser Cys Asn Pro Val Asn
                325                 330                 335 gca agt ggg ttc agg cca tac aag aga tgc cta tca gaa aga gaa gta      1056
Ala Ser Gly Phe Arg Pro Tyr Lys Arg Cys Leu Ser Glu Arg Glu Val
            340                 345                 350 aca tca tca ttg acg ctg gta gct tca gat gaa aag aaa agc caa aga      1104
Thr Ser Ser Leu Thr Leu Val Ala Ser Asp Glu Lys Lys Ser Gln Arg
        355                 360                 365 gca cgt ata tgc tag                                                   1119
Ala Arg Ile Cys
    370
```

<210> SEQ ID NO 4
<211> LENGTH: 372
<212> TYPE: PRT
<213> ORGANISM: Arabidopsis thaliana

<400> SEQUENCE: 4

```
Met Leu Cys Phe Val Arg Phe Gln Ala Gly Phe Val Arg Ile Ile Val
1               5                   10                  15

Ala Ala Arg Lys Arg Phe Arg Tyr Phe Leu Met Ala Ala Glu Asp Arg
            20                  25                  30

Ser Glu Glu Leu Ser Ser Asn Val Glu Asn Gly Ser Cys Asn Ser Asn
        35                  40                  45

Glu Gly Ile Asn Pro Glu Thr Ser Ser His Trp Ile Glu Asn Val Val
    50                  55                  60

Lys Val Arg Lys Pro Tyr Thr Val Thr Lys Gln Arg Glu Lys Trp Ser
65                  70                  75                  80

Glu Glu Glu His Asp Arg Phe Leu Glu Ala Ile Lys Leu Tyr Gly Arg
                85                  90                  95

Gly Trp Arg Gln Ile Gln Glu His Ile Gly Thr Lys Thr Ala Val Gln
            100                 105                 110

Ile Arg Ser His Ala Gln Lys Phe Phe Ser Lys Met Ala Gln Glu Ala
        115                 120                 125

Asp Ser Arg Ser Glu Gly Ser Val Lys Ala Ile Val Ile Pro Pro Pro
    130                 135                 140

Arg Pro Lys Arg Lys Pro Ala His Pro Tyr Pro Arg Lys Ser Pro Val
145                 150                 155                 160

Pro Tyr Thr Gln Ser Pro Pro Asn Leu Ser Ala Met Glu Lys Gly
                165                 170                 175

Thr Lys Ser Pro Thr Ser Val Leu Ser Ser Phe Gly Ser Glu Asp Gln
            180                 185                 190

Val Asn Arg Cys Ser Ser Pro Asn Ser Cys Thr Ser Asp Ile Gln Ser
```

```
                      195                 200                 205

Ile Gly Ala Thr Ser Ile Asp Lys Lys Asn Asn Tyr Thr Thr Ser Lys
    210                 215                 220

Gln Pro Phe Lys Asp Asp Ser Asp Ile Gly Ser Thr Pro Ile Ser Ser
225                 230                 235                 240

Ile Thr Leu Phe Gly Lys Ile Val Leu Val Ala Glu Glu Ser His Lys
            245                 250                 255

Pro Ser Ser Tyr Asn Asp Asp Leu Lys Gln Met Thr Cys Gln Glu
                260                 265                 270

Asn His Tyr Ser Gly Met Leu Val Asp Thr Asn Leu Ser Leu Gly Val
                275                 280                 285

Trp Glu Thr Phe Cys Thr Gly Ser Asn Ala Phe Gly Ser Val Thr Glu
    290                 295                 300

Ala Ser Glu Asn Leu Glu Lys Ser Ala Glu Pro Ile Ser Ser Ser Trp
305                 310                 315                 320

Lys Arg Leu Ser Ser Leu Glu Lys Gln Gly Ser Cys Asn Pro Val Asn
                325                 330                 335

Ala Ser Gly Phe Arg Pro Tyr Lys Arg Cys Leu Ser Glu Arg Glu Val
                340                 345                 350

Thr Ser Ser Leu Thr Leu Val Ala Ser Asp Glu Lys Lys Ser Gln Arg
            355                 360                 365

Ala Arg Ile Cys
    370

<210> SEQ ID NO 5
<211> LENGTH: 498
<212> TYPE: DNA
<213> ORGANISM: Arabidopsis thaliana
<220> FEATURE:
<221> NAME/KEY: CDS
<222> LOCATION: (1)..(498)

<400> SEQUENCE: 5 atg gat tcg aaa aat gga att aac aac agc caa aag gca aga agg act      48
Met Asp Ser Lys Asn Gly Ile Asn Asn Ser Gln Lys Ala Arg Arg Thr
1               5                   10                  15 cca aaa gac cgc cat ttg aaa att ggt ggc cgt gat cgt cgc att cgg      96
Pro Lys Asp Arg His Leu Lys Ile Gly Gly Arg Asp Arg Arg Ile Arg
                20                  25                  30 atc ccg ccg agt gtt gct ccc caa cta ttt aga ttg aca aaa gaa ctc     144
Ile Pro Pro Ser Val Ala Pro Gln Leu Phe Arg Leu Thr Lys Glu Leu
            35                  40                  45 ggc ttt aaa acc gat ggt gaa act gtc agt tgg ctc ctc cag aat gcc     192
Gly Phe Lys Thr Asp Gly Glu Thr Val Ser Trp Leu Leu Gln Asn Ala
    50                  55                  60 gag cct gcc att ttc gca gcc acg gga cat ggt gtc acc acc acc tcc     240
Glu Pro Ala Ile Phe Ala Ala Thr Gly His Gly Val Thr Thr Thr Ser
65                  70                  75                  80 aat gaa gat atc cag cca aat agg aat ttt cct agt tac acc ttt aat     288
Asn Glu Asp Ile Gln Pro Asn Arg Asn Phe Pro Ser Tyr Thr Phe Asn
                85                  90                  95 ggt gat aat att agt aat aac gtt ttc cct tgt acg gtt gta aat act     336
Gly Asp Asn Ile Ser Asn Asn Val Phe Pro Cys Thr Val Val Asn Thr
                100                 105                 110 ggt cat cgt cag atg gtg ttt ccg gtt tct aca atg aca gat cat gca     384
Gly His Arg Gln Met Val Phe Pro Val Ser Thr Met Thr Asp His Ala
            115                 120                 125 cct tca act aat tac agt act att agt gat aat tac aat tcc acc ttt     432
```

```
Pro Ser Thr Asn Tyr Ser Thr Ile Ser Asp Asn Tyr Asn Ser Thr Phe
        130                 135                 140 aat ggt aat gct acc gcc agt gat aca aca tca gca gca aca aca aca    480
Asn Gly Asn Ala Thr Ala Ser Asp Thr Thr Ser Ala Ala Thr Thr Thr
145                 150                 155                 160 gcc aca acc aca gtt tga                                            498
Ala Thr Thr Thr Val
            165

<210> SEQ ID NO 6
<211> LENGTH: 165
<212> TYPE: PRT
<213> ORGANISM: Arabidopsis thaliana

<400> SEQUENCE: 6

Met Asp Ser Lys Asn Gly Ile Asn Asn Ser Gln Lys Ala Arg Arg Thr
1               5                   10                  15

Pro Lys Asp Arg His Leu Lys Ile Gly Gly Arg Asp Arg Ile Arg
            20                  25                  30

Ile Pro Pro Ser Val Ala Pro Gln Leu Phe Arg Leu Thr Lys Glu Leu
        35                  40                  45

Gly Phe Lys Thr Asp Gly Glu Thr Val Ser Trp Leu Leu Gln Asn Ala
    50                  55                  60

Glu Pro Ala Ile Phe Ala Ala Thr Gly His Gly Val Thr Thr Thr Ser
65                  70                  75                  80

Asn Glu Asp Ile Gln Pro Asn Arg Asn Phe Pro Ser Tyr Thr Phe Asn
                85                  90                  95

Gly Asp Asn Ile Ser Asn Asn Val Phe Pro Cys Thr Val Val Asn Thr
            100                 105                 110

Gly His Arg Gln Met Val Phe Pro Val Ser Thr Met Thr Asp His Ala
        115                 120                 125

Pro Ser Thr Asn Tyr Ser Thr Ile Ser Asp Asn Tyr Asn Ser Thr Phe
    130                 135                 140

Asn Gly Asn Ala Thr Ala Ser Asp Thr Thr Ser Ala Ala Thr Thr Thr
145                 150                 155                 160

Ala Thr Thr Thr Val
            165

<210> SEQ ID NO 7
<211> LENGTH: 30
<212> TYPE: DNA
<213> ORGANISM: Artificial Sequence
<220> FEATURE:
<223> OTHER INFORMATION: Synthetic oligonucleotide primer

<400> SEQUENCE: 7
gatgataagc aaggatccaa gatcgagttt                                   30

<210> SEQ ID NO 8
<211> LENGTH: 30
<212> TYPE: DNA
<213> ORGANISM: Artificial Sequence
<220> FEATURE:
<223> OTHER INFORMATION: Synthetic oligonucleotide primer

<400> SEQUENCE: 8
gccttgatat tgaaggtgag aactcatcat                                   30

<210> SEQ ID NO 9
<211> LENGTH: 13
```

```
<212> TYPE: PRT
<213> ORGANISM: Artificial Sequence
<220> FEATURE:
<223> OTHER INFORMATION: Synthetic oligonucleotide primer

<400> SEQUENCE: 9

Gly Leu Asp Leu Asp Leu Glu Leu Arg Leu Gly Phe Ala
1               5                   10

<210> SEQ ID NO 10
<211> LENGTH: 30
<212> TYPE: DNA
<213> ORGANISM: Artificial Sequence
<220> FEATURE:
<223> OTHER INFORMATION: Synthetic oligonucleotide primer

<400> SEQUENCE: 10
gatggccgct gaggatcgaa gtgaggaact                                      30

<210> SEQ ID NO 11
<211> LENGTH: 30
<212> TYPE: DNA
<213> ORGANISM: Artificial Sequence
<220> FEATURE:
<223> OTHER INFORMATION: Synthetic oligonucleotide primer

<400> SEQUENCE: 11
gcatatacgt gctctttggc ttttcttttc                                      30

<210> SEQ ID NO 12
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 12
atggattcga aaatggaat taac                                             24

<210> SEQ ID NO 13
<211> LENGTH: 23
<212> TYPE: DNA
<213> ORGANISM: Artificial Sequence
<220> FEATURE:
<223> OTHER INFORMATION: Synthetic oligonucleotide primer

<400> SEQUENCE: 13
aactgtggtt gtggctgttg ttg                                             23

<210> SEQ ID NO 14
<211> LENGTH: 21
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(10)
<223> OTHER INFORMATION: Xaa is any amino acid
<220> FEATURE:
<221> NAME/KEY: misc_feature
<222> LOCATION: (14)..(14)
<223> OTHER INFORMATION: Xaa is Asn or Glu
<220> FEATURE:
<221> NAME/KEY: misc_feature
<222> LOCATION: (16)..(21)
<223> OTHER INFORMATION: Xaa is any amino acid

<400> SEQUENCE: 14
```

```
Xaa Xaa Xaa Xaa Xaa Xaa Xaa Xaa Xaa Xaa Leu Asp Leu Xaa Leu Xaa
1               5                   10                  15

Xaa Xaa Xaa Xaa Xaa
            20

<210> SEQ ID NO 15
<211> LENGTH: 21
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(10)
<223> OTHER INFORMATION: Xaa is any amino acid
<220> FEATURE:
<221> NAME/KEY: misc_feature
<222> LOCATION: (15)..(15)
<223> OTHER INFORMATION: Xaa is Phe or Ile
<220> FEATURE:
<221> NAME/KEY: misc_feature
<222> LOCATION: (16)..(21)
<223> OTHER INFORMATION: Xaa is any amino acid

<400> SEQUENCE: 15

Xaa Xaa Xaa Xaa Xaa Xaa Xaa Xaa Xaa Xaa Phe Asp Leu Asn Xaa Xaa
1               5                   10                  15

Xaa Xaa Xaa Xaa Xaa
            20

<210> SEQ ID NO 16
<211> LENGTH: 19
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (6)..(6)
<223> OTHER INFORMATION: Xaa is Glu, Gln or Asp
<220> FEATURE:
<221> NAME/KEY: misc_feature
<222> LOCATION: (10)..(19)
<223> OTHER INFORMATION: Xaa is any amino acid

<400> SEQUENCE: 16

Leu Asp Leu Asp Leu Xaa Leu Arg Leu Xaa Xaa Xaa Xaa Xaa Xaa Xaa
1               5                   10                  15

Xaa Xaa Xaa

<210> SEQ ID NO 17
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa represents Glu, Gln, or Asp

<400> SEQUENCE: 17

Asp Leu Xaa Leu Arg Leu
1               5

<210> SEQ ID NO 18
<211> LENGTH: 6
<212> TYPE: PRT
```

```
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa represents Asp, Asn, Glu, Gln, Thr, or Ser
<220> FEATURE:
<221> NAME/KEY: misc_feature
<222> LOCATION: (3)..(3)
<223> OTHER INFORMATION: Xaa represents Asp, Gln, Asn, Arg, Glu, Thr,
      Ser, or His
<220> FEATURE:
<221> NAME/KEY: misc_feature
<222> LOCATION: (5)..(5)
<223> OTHER INFORMATION: Xaa represents Arg, Gln, Asn, Thr, Ser, His,
      Lys, or Asp

<400> SEQUENCE: 18

Xaa Leu Xaa Leu Xaa Leu
1               5

<210> SEQ ID NO 19
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa represents Asp, Asn, Glu, Gln, Thr, or Ser
<220> FEATURE:
<221> NAME/KEY: misc_feature
<222> LOCATION: (3)..(3)
<223> OTHER INFORMATION: Xaa represents Asp, Gln, Asn, Arg, Glu, Thr,
      Ser, or His
<220> FEATURE:
<221> NAME/KEY: misc_feature
<222> LOCATION: (5)..(5)
<223> OTHER INFORMATION: Xaa represents Gln, Asn, Thr, Ser, His, Lys, or
      Asp

<400> SEQUENCE: 19

Xaa Leu Xaa Leu Xaa Leu
1               5

<210> SEQ ID NO 20
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa represents Asp, Asn, Glu, Gln, Thr, or Ser
<220> FEATURE:
<221> NAME/KEY: misc_feature
<222> LOCATION: (3)..(3)
<223> OTHER INFORMATION: Xaa represents Asn, Arg, Thr, Ser, or His

<400> SEQUENCE: 20

Xaa Leu Xaa Leu Arg Leu
1               5

<210> SEQ ID NO 21
<211> LENGTH: 6
<212> TYPE: PRT
<213> ORGANISM: Artificial Sequence
<220> FEATURE:
<223> OTHER INFORMATION: Synthetic peptide
<220> FEATURE:
```

```
<221> NAME/KEY: misc_feature
<222> LOCATION: (1)..(1)
<223> OTHER INFORMATION: Xaa represents Asn, Glu, Gln, Thr, or Ser
<220> FEATURE:
<221> NAME/KEY: misc_feature
<222> LOCATION: (3)..(3)
<223> OTHER INFORMATION: Xaa represents Asp, Gln, Asn, Arg, Glu, Thr,
      Ser, or His

<400> SEQUENCE: 21

Xaa Leu Xaa Leu Arg Leu
1               5
```

US 9,816,099 B2

GENE FOR INCREASING PLANT WEIGHT AND METHOD FOR USING THE SAME

This is a Divisional of application Ser. No. 13/376,138, filed Dec. 2, 2011, which is a National Stage Entry of International Application No. PCT/JP2010/003761, filed Jun. 4, 2010, which claims priority to Japanese Patent Application No. 2009-135309, filed Jun. 4, 2009, the contents of all of which are incorporated herein by reference in their entirety.

TECHNICAL FIELD

The present invention relates to a gene for increasing plant weight and a method for using the same.

BACKGROUND ART

The term "biomass" generally refers to the total amount of organisms that inhabit or organic matter that exists in a given area. Particularly regarding plants, plant biomass refers to the dry weight of the plants that exists in a given area. The unit of such biomass is quantified using mass or energy level. The expression "biomass" is a synonym of a term "an amount of an organism." In the case of plant biomass, the term "standing crop" is also used. Plant biomass is generated by fixing carbon dioxide in the air using solar energy, so that it can be captured as so-called carbon neutral energy. Therefore, an increase in such plant biomass has effects of terrestrial environmental protection, prevention of global warming, and reduction of greenhouse gas emissions. Hence, technologies for increasing plant biomass have high industrial importance.

In addition, plants are cultivated for their partial tissues (e.g., seeds, roots, and leaf stems) or for production of various substances such as fats and oils. For example, as fats and oils produced by plants, soybean oil, sesame oil, olive oil, coconut oil, rice oil, cottonseed oil, sunflower oil, corn oil, safflower oil, palm oil, rapeseed oil, and the like are conventionally known and broadly used for household or industrial applications. Also, fats and oils produced by plants are used as raw materials for biodiesel fuel or bioplastics, allowing the applicability thereof to spread as alternatives to petroleum as energy sources.

Under such circumstances, improvement of productivity per unit of cultivated area is required for industrially successful fat and oil production using plants. Assuming that the number of cultivated plants per unit of cultivated area remains constant, it is un-derstood that improvement in fat and oil production per individual plant is needed. When fats and oils are collected from seeds harvested from plant bodies, it is expected that improved fat and oil production per individual plant can be achieved by a technology for improving the seed yield per individual plant, a technology for improving the fat and oil contents in seeds, or the like.

Technologies for increasing the fat and oil production from plant seeds are mainly divided into those based on improved cultivation techniques and those based on development of cultivars for increased fat and oil production. Methods for developing cultivars with increased fat and oil production are mainly divided into conventional breeding techniques mainly composed of mating technologies and molecular breeding methods using genetic recombination. As technologies for increased fat and oil production using genetic recombination, A) a technology that involves altering the synthesis system for seed triacylglycerol (TAG), which is a major ingredient of plant fats and oils, and B) a technology that involves altering various control genes for con-trolling plant morphological formation, metabolism, and the expression of genes involved therein are known.

Possible examples of method A) above include methods for increasing the amount of TAG synthesized using sugar produced by photosynthesis as a raw material. These include (1) a method that involves enhancing activity for the synthesis of fatty acid or glycerol, which is a component of TAG from sugar, and (2) a method for enhancing the reaction by which TAG is synthesized from glycerol and fatty acid. Concerning such methods, the following technologies have been reported as technologies using genetic engineering techniques. An example of (1) is provided in a report (Plant Physiology (1997) Vol. 11, pp. 75-81) wherein it was noted that seed fat and oil contents were improved by 5% via overexpression of cytoplasmic acetyl-coenzyme A carboxylase (ACCase) of *Arabidopsis thaliana* in rapeseed plastids. Also, an example of (2) is provided in a report (Plant Physiology (2001), Vol. 126, pp. 861-874) concerning a technology for increased fat and oil production via overexpression of DGAT (diacylglycerol acyltransferase), which undergoes acyl transfer to the sn-3 position of diacylglycerol. In the report regarding this method, fat and oil contents and seed weights were increased as the DGAT expression levels were increased, so that the number of seeds per individual plant could increase. *Arabidopsis thaliana* seed fat and oil content was increased by 46% with the use of this method, and the fat and oil content per individual plant was increased by approximately 125% at maximum.

In addition, a possible example of method B) above is a method that involves con-trolling the expression of a transcriptional factor gene involved in control of the expression of a biosynthesis system enzyme gene. An example thereof is given in WO01/36597. In WO01/36597, a technique was employed that involves producing recombinant plants through exhaustive overexpression or knock-out of a transcriptional factor and then selecting a gene that enhances seed fat and oil contents. WO01/36597 states that seed fat and oil contents were increased by 23% through overexpression of the ERF subfamily B-4 transcriptional factor gene. However, WO01/36597 does not state increases or decreases in the fat and oil content per individual plant. Plant J. (2004) 40, 575-585 describes that seed fat and oil contents can be improved by overexpression of WRINKLED1, the transcriptional factor containing the AP2/EREB domain.

Furthermore, when a hydrocarbon component such as cellulose contained in plant bodies is glycosylated and then alcohol is produced by fermentation, fat and oil components contained in plants become impurities that can cause reduced glycosylation efficiency in a glycosylation step. Therefore, if fat and oil contents can be decreased, glycosylation efficiency in a glycosylation step can be improved and thus improved alcohol productivity can be expected. For example, Plant J. (2004) 40, 575-585 discloses that in the case of the WRI1/ASML1 (AP2 family transcriptional factor: AGI-code: AT3g54320)-deficient line, seeds were wrinkled and the fat and oil contents were decreased. Furthermore, WO01/35727 discloses the following: the seed fat and oil content was decreased by 13% through overexpression of AT3g23250 (MYB15): the seed fat and oil content was decreased by 12% through overexpression of AT1g04550 (IAA 12); and the seed fat and oil content was decreased by 16% through overexpression of AT1g66390 (MYB90).

Moreover, several attempts to improve biomass have been carried out. For example, Proc. Natl. Acad. Sci. U.S.A., 2000, Jan. 18: 97(2), 942-947 discloses that plant organ cell number, organ size, and individual plant size were increased through overexpression of the At4g37750 (AINTEGUMENTA) gene. Similarly. Plant Cell, 2003, Sep.; 15(9), 1951-1961 discloses that when overexpression of At2g44080 (ARL) was caused, plant organ cell number, organ size, and individual plant size were increased. Also, Plant J. (2006) July, 47(1), 1-9 discloses that cell division was activated through overexpression of At1g15690 (AVP1), so that individual plant size was increased. Furthermore. Development 2006, January; 133 (2), 251-261 reports that when At5g62000 (ARF2) was deficient, seeds and flower organs became larger in size.

However, although the above molecular breeding methods for improvement of various characters have been developed, no technology has reached a practical level that would allow both increased biomass and improved or decreased fat and oil productivity.

This may be because truly excellent genes remain undiscovered and because novel recombinant cultivars effective at test stages are unable to exert effects as desired at practical stages under various natural environments. Furthermore, regarding quantitative character such as increased plant weight and productivity of a target substance, many genes are involved in various steps, ranging from control systems to metabolic systems. Hence, it has been difficult to discover and develop a truly excellent useful gene for improvement of quantitative characters. Objects required to address these problems are: discovery of a novel gene with drastically high effects; and development of a gene capable of exerting effects under practical environmental conditions, even if its effect levels are equivalent to those of conventional genes. Furthermore, it is expected that practical levels would be achieved by the simultaneous use of a plural number of genes, even if each of the genes has effect level equivalent to or lower than those of conventional genes. Accordingly, another object is to develop a plurality of genes having different functions.

DISCLOSURE OF THE INVENTION

Object to be Achieved by the Invention

In view of the above-described circumstances, an object of the invention is to search for a gene having novel functions by which plant weight (that is, plant biomass level) can be increased and by means of which substance productivity can be increased or decreased, so as to provide a technology capable of improving the properties of plant bodies.

Means to Achieve the Object

As a result of intensive studies to achieve the above objects, the present inventors have discovered that various quantitative characters can be improved through expression of a chimeric protein in which a specific transcriptional factor is fused to a functional peptide (hereinafter, this may also be referred to as a repressor domain) that converts an arbitrary transcriptional factor to a transcriptional repression factor. Particularly, the present inventors have discovered that plant weight (that is, plant biomass level) can be increased and that substance productivity can be increased or decreased. Thus, the present inventors have completed the present invention.

The plant body according to the present invention expresses a chimeric protein wherein a transcriptional factor comprising any one of the following proteins (a) to (c) is fused to a functional peptide that converts an arbitrary transcriptional factor to a transcriptional repression factor:

(a) a protein comprising the amino acid sequence shown in SEQ ID NO: 2, 4, or 6;

(b) a protein comprising an amino acid sequence that has a deletion, a substitution, an addition, or an insertion of one or a plurality of amino acids with respect to the amino acid sequence shown in SEQ ID NO: 2, 4, or 6 and having activity of accelerating transcription; and (c) a protein encoded by a polynucleotide hybridizing under stringent conditions to a polynucleotide that comprises a nucleotide sequence complementary to the nucleotide sequence shown in SEQ ID NO: 1, 3, or 5 and having activity of accelerating transcription.

In the plant body according to the present invention, the transcriptional control activity and particularly the activity of accelerating transcription of a predetermined transcriptional factor is preferably suppressed by fusion of a functional peptide. Examples of the above functional peptide include the peptides represented by the following formulae (1) to (8), respectively:

X1-Leu-Asp-Leu-X2-Leu-X3 (1)

(wherein X1 denotes 0 to 10 amino acid residues. X2 denotes Asn or Glu, and X3 denotes at least 6 amino acid residues.)

Y1-Phe-Asp-Leu-Asn-Y2-Y3 (2)

(wherein Y1 denotes 0 to 10 amino acid residues, Y2 denotes Phe or Ile, and Y3 denotes at least 6 amino acid residues.)

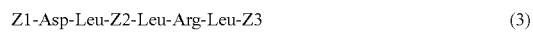
Z1-Asp-Leu-Z2-Leu-Arg-Leu-Z3 (3)

(wherein Z1 denotes Leu, Asp-Leu, or Leu-Asp-Leu, Z2 denotes Glu, Gin, or Asp, and Z3 denotes 0 to 10 amino acid residues.)

Asp-Leu-Z4-Leu-Arg-Leu (4)

(wherein Z4 denotes Glu, Gin, or Asp.)

alpha1-Leu-beta1-Leu-gamma1-Leu (5)

alpha1-Leu-beta1-Leu-gamma2-Leu (6)

alpha1-Leu-beta2-Leu-Arg-Leu (7)

alpha2-Leu-beta1-Leu-Arg-Leu (8)

(and in the formulae (5) to (8), alpha1 denotes Asp, Asn, Glu, Gin, Thr, or Ser, alpha2 denotes Asn, Glu, Gin, Thr, or Ser, beta1 denotes Asp, Gin, Asn, Arg, Glu. Thr, Ser, or His, beta2 denotes Asn, Arg, Thr, Ser, or His, gamma1 denotes Arg, Gin. Asn, Thr, Ser, His, Lys, or Asp, and gamma2 denotes Gin, Asn, Thr, Ser, His, Lys, or Asp.) The plant weight of the plant body according to the present invention is significantly improved. Here, the term "significantly" refers to a situation in which the plant weight is increased to a statistically significant extent compared with the plant weight of a plant body not expressing the above chimeric protein.

Also, in the plant body according to the present invention, substance productivity per individual plant, and particularly, the productivity of fats and oils contained in seeds, is significantly improved or decreased. Examples of specific tissues include seeds. Here, the term "significantly" refers to a situation in which substance productivity is increased or decreased to a statistically significant extent compared with substance productivity in a plant body not expressing the above chimeric protein.

Meanwhile, according to the present invention, the above-described chimeric protein, a gene encoding the chimeric protein, an expression vector containing the gene, and a transformant containing the gene can be provided.

Effect of the Invention

The plant body according to the present invention has improved plant weight; that is, it exhibits an improved biomass level. Therefore, by the use of the plant body according to the present invention, improvement can be achieved in terms of productivity of a substance that is produced using a plant body itself or a part of a plant body as a raw material, such as bioalcohol. Thus, a substance of interest can be produced at low cost according to the present invention.

BEST MODE OF CARRYING OUT THE INVENTION

The present invention will be described in detail as follows.

The plant body according to the present invention expresses a chimeric protein in which a predetermined transcriptional factor is fused to a functional peptide that converts an arbitrary transcriptional factor to a transcriptional repression factor and has a significantly improved plant weight (that is, a plant biomass level) compared with that of wild-type plant bodies. Specifically, the plant body according to the present invention is produced by causing a desired (target) plant to express a transcriptional factor in the form of a chimeric protein with the above functional peptide, so as to significantly improve the plant biomass level of the plant. Also, the plant body of the present invention has significantly improved or decreased substance productivity per individual plant and particularly improved productivity of fats and oils contained in seeds, compared with wild-type plant bodies.

In particular, it is preferable that, in the plant body according to the present invention, the activity of accelerating transcription of the transcriptional factor is suppressed through fusion of the factor with the above functional peptide. That is, preferably, the plant body according to the present invention is characterized in that, as a result of expression of a chimeric protein in which the above functional peptide is fused to a transcriptional factor, the transcriptional repression effect resulting from the above functional peptide appears as a dominant character.

Here, the expression. "improvement of the plant weight" is synonymous with namely, "increased biomass," that is; increased biomass per given area. Two technologies contribute to increase the biomass per given area: a technology for increasing the degree of dense planting (the number of plants per given area) and a technology for increasing the weight or energy level per individual plant. Hence, not only the dry weight per given area, but also the dry weight per individual plant can also be evaluated as plant biomass.

Accordingly, the biomass as defined in the present invention may be dry plant weight per individual plant, the dry weight (per individual plant) of the above ground part of a plant, or the weight of a specific tissue. Here, the term "tissue weight per individual plant" refers to the weight of at least one or more types of tissue selected from among seeds, roots, leaves, stems, flowers, pollens, and the like, composing a plant.

The term "substance productivity per individual plant" refers to the content per unit volume of one of various substances generated by plants. A substance to be used herein is not particularly limited and may be a substance that is originally generated by a plant body or a substance that is not originally generated by a plant body but can be generated by the plant body as a result of genetic engineering, or the like.

Particularly, if the content of a product of interest per tissue is increased, the present invention is industrially useful, since purification cost and transportation cost can be reduced. Particularly, a product of interest may be lignocellulose the weight of which accounts for most weight of the plant or plant oil that is industrially used as seed oil. Plant oil may be simple lipid that is an ester of fatty acid and alcohol, complex lipid containing phosphorus, sugar, nitrogen, and the like, or fatty acid itself. Alcohol of simple lipid may be high-molecular-weight higher alcohol or polyalcohol such as glycerol (glycerine). Fatty acid of simple lipid may be saturated fatty acid or un-saturated fatty acid, as well as, special fatty acid containing a hydroxyl group and an epoxy group. Simple lipid that is an ester of glycerol and fatty acid may be monoacyl-glycerol, diacylglycerol, or triacylglycerol.

Meanwhile, depending on the application of a plant bcody, a predetermined substance contained in the plant body may be an impurity. Therefore, the lower the productivity of a predetermined substance, the more decreased impurity content, leading to high industrial usefulness. For example, when lignocellulose contained in a plant body is glycosylated, a fat and oil component contained in the plant body as an impurity may adversely affect glycosylation efficiency. Hence, if the productivity of fats and oils is decreased, the efficiency of a glycosylation step of the production process for bioalcohol or the like using plant bodies can be improved.

The following explanation is given by exemplifying fats and oils as substances that improve or decrease productivity, but the technical scope of the present invention is not limited thereto. The present invention is similarly applicable to substances to be generated by plants other than fats and oils.

The plant body to be used herein is not particularly limited. Any plant can be a target. Particularly preferably such target plants are those conventionally used for production of fats and oils. Examples of such target plants include soybean, sesame, olive oil, coconut, rice, cotton, sunflower, corn, sugarcane, jatropha, palm coconut, tobacco, safflower, and rapeseed. Also, another possible target plant is *Arabidopsis thaliana* that has been broadly used as a model organism for plant gene analysis, for which a method for gene expression analysis has been established.

Also, the transcriptional repression is the activity of a chimeric protein comprising a transcriptional factor, by which a cis sequence to be recognized by the transcriptional factor or a cis sequence analogous thereto in another transcriptional factor is recognized, so as to aggressively suppress downstream gene expression. Transcriptional repression can also be referred to as a transcriptional repression factor. A technique for undergoing transcriptional repression possessed as activity by a chimeric protein comprising a transcriptional factor is not particularly limited. Particularly, a method for constructing a chimeric protein (fusion protein) to which a repressor domain sequence or an SRDX sequence has been added is most preferable.

A repressor domain sequence in this technique is an amino acid sequence composing a peptide that converts an arbitrary transcriptional factor to a transcriptional repression factor and the present inventors have discovered various types thereof. Regarding methods using repressor domain sequences, JP Patent Publication (Kokai) No. 2001-269177 A, JP Patent Publication (Kokai) No. 2001-269178 A, JP Patent Publication (Kokai) No. 2001-292776 A, JP Patent Publication (Kokai) No. 2001-292777 A, JP Patent Publication (Kokai) No. 2001-269176 A, JP Patent Publication (Kokai) No. 2001-269179 A, International Patent Publication WO03/055903, Pamphlet, Ohta, M., Matsui. K., Hiratsu, K., Shinshi, H. and Ohme-Takagi. M., The Plant Cell, Vol. 13, 1959-1968, August, 2001, and Hiratsu, K., Ohta, M. Matsui, K., Ohme-Takagi, M., FEBS Letters 514 (2002) 351-354 can be referred to, for example. A repressor domain sequence is excised from Class II ERF (Ethylene Responsive Element Binding Factor) protein or a plant zinc finger protein (e.g., *Arabidopsis thaliana* SUPERMAN protein) and has an extremely simple structure.

Examples of a transcriptional factor that is expressed in the form of a chimeric protein include a transcriptional factor (hereinafter, simply referred as the "transcriptional factor At3g04070." The same applies to the following examples) specified under AGI code At3g04070 of *Arabidopsis thaliana*, the transcriptional factor At1g18330, and the transcriptional factor At3g45150. In addition, the transcriptional factor At3g04070 is a transcriptional factor belonging to the NAC family. The transcriptional factor At1g18330 is a transcriptional factor belonging to the single MYB (R3-MYB) family. The transcriptional factor At3g45150 is a transcriptional factor belonging to the TCP family. The amino acid sequence of the transcriptional factor At3g04070 is shown in SEQ ID NO: 2 and the nucleotide sequence of a gene encoding the transcriptional factor At3g04070 is shown in SEQ ID NO: 1. The amino acid sequence of the transcriptional factor At1g18330 is shown in SEQ ID NO: 4 and the nucleotide sequence of a gene encoding the transcriptional factor At1g18330 is shown in SEQ ID NO: 3. The amino acid sequence of the transcriptional factor At3g45150 is shown in SEQ ID NO: 6 and the nucleotide sequence of a gene encoding the transcriptional factor At3g45150 is shown in SEQ ID NO: 5.

Moreover, the transcriptional factor At3g04070, the transcriptional factor At1g18330, and the transcriptional factor At3g45150 that are targets of a chimeric protein are not limited to those comprising amino acid sequences shown in SEQ ID NOS: 2, 4, and 6, respectively. Such a target transcriptional factor may comprise an amino acid sequence that has a deletion, a substitution, an addition, or an insertion of one or a plurality of amino acids with respect to the amino acid sequence shown in SEQ ID NO: 2, 4, or 6 and having activity of accelerating transcription. Here the term "a plurality of amino acids" refers to 1 to 20, preferably 1 to 10, more preferably 1 to 7, further more preferably 1 to 5, and particularly preferably 1 to 3 amino acids, for example. In addition, a deletion, a substitution, or an addition of amino acids can be performed by altering a nucleotide sequence encoding the above transcriptional factor by techniques known in the art. A mutation can be introduced into a nucleotide sequence by a known technique such as the Kunkel method or the Gapped duplex method or a method according thereto. For example, a mutation is introduced using a mutagenesis kit using site-directed mutagenesis (e.g., Mutant-K and Mutant-G (both of which are trade names, manufactured by TAKARA Bio)) or using a LA PCR in vitro Mutagenesis series kit (trade name, manufactured by TAKARA Bio). Also, a mutagenesis method may be a method that uses a chemical agent for mutation represented by EMS (ethylmethane sulfonate), 5-bromouracil, 2-aminopurine, hydroxylamine, N-methyl-N'-nitro-N-nitrosoguanidine, or other carcinogenic compounds or a method based on radiation treatment typically using an X ray, an alpha ray, a beta ray, a gamma-ray, or an ion beam or ultraviolet {UV} treatment.

Furthermore, examples of a transcriptional factor that is a target of a chimeric protein are not limited to the transcriptional factor At3g04070, the transcriptional factor At1g18330, and the transcriptional factor At3g45150 of *Arabidopsis thaliana*. Examples thereof also include transcriptional factors (hereinafter, referred as homologous transcriptional factors) having the same functions in plants (e.g., the above-mentioned plants) other than *Arabidopsis thaliana*. Transcriptional factors homologous to the transcriptional factor At3g04070, the transcriptional factor At1g18330, and the transcriptional factor At3g45150 can be searched for from plant genome information to be searched based on the amino acid sequence of the transcriptional factor At3g04070, the transcriptional factor At1g 18330, or the transcriptional factor At3g45150 or the nucleotide sequence of each gene thereof, as long as the plant genome information has been revealed. At this time, a homologous transcriptional factor is searched for as an amino acid sequence having 70% or more, preferably 80% or more, more preferably 90% or more, and most preferably 95% or more homology with respect to the amino acid sequence of the transcriptional factor At3g04070, the transcriptional factor At1g18330, or the transcriptional factor At3g45150. Here, the value of homology refers to a value found using database that store a computer program mounting blast algorithm, gene sequence information, and default setting.

Moreover, when plant genome information is unknown, a homologous gene can be identified by extracting a genome from a target plant or constructing a cDNA library of a target plant, and then isolating a genomic region or cDNA hybridizing under stringent conditions to at least a part of a gene encoding the transcriptional factor At3g04070, the transcriptional factor At1g18330, or the transcriptional factor At3g45150. Here, the term "stringent conditions" refers to conditions where a so-called specific hybrid is formed, but no non-specific hybrid is formed. For example, hybridization is performed at 45 degrees C. using 6×SSC (sodium chloride/sodium citrate) and then washing is performed under conditions of 50 degrees C.-65 degrees C., 0.2-1× SSC, and 0.1% SDS. Alternatively, examples thereof include hybridization at 65 degrees C.-70 degrees C. using 1×SSC followed by washing at 65 degrees C.-70 degrees C. using 0.3×SSC. Hybridization can be performed by a conventionally known method such as a method described in J. Sambrook et al. Molecular Cloning, A Laboratory Manual, 2nd Ed., Cold Spring Harbor Laboratory (1989).

The plant body according to the present invention is characterized in that as a result of expression of the above-described chimeric protein of a transcriptional factor and a functional peptide, the plant weight (that is, a biomass level) is significantly improved, and that fat and oil production is significantly changed (improved or decreased). Particularly, the plant body according to the present invention is characterized in that, through preparation of such a chimeric protein, a target transcriptional factor is expressed in the form of the chimeric protein with suppressed activity of accelerating transcription, and transcriptional repression activity is expressed to recognize a cis sequence having homology with a cis sequence that is recognized by the target transcriptional factor. Furthermore, the plant body is also characterized in that the plant weight (that is, biomass level) is significantly improved, and that fat and oil production is significantly changed (improved or decreased) by varying the affinity specificity of the target transcriptional factor for another factor, nucleic acid, lipid, or carbohydrate. At this time, in the above plant body, a chimeric protein may be prepared via alteration of an endogenous transcriptional factor or a gene encoding a chimeric protein may be introduced and then the gene is expressed.

As an example, a preferable technique involves introducing a gene encoding a chimeric protein (fusion protein) in which the above-described transcriptional factor is fused to a functional peptide that converts an arbitrary transcriptional factor to a transcriptional repression factor into a target plant and then causing expression of the chimeric protein (fusion protein) within the plant.

The term "transcriptional factor with suppressed activity of accelerating transcription" described in this Description is not particularly limited and refers to a transcriptional factor having significantly decreased activity of accelerating transcription that is originally possessed by the transcriptional factor. Also, the term "functional peptide that converts an arbitrary transcriptional factor to a transcriptional repression factor" refers to, when it is fused to an arbitrary transcriptional factor to form a chimeric protein, a peptide that has functions so that the resulting transcriptional factor has significantly decreased activity of accelerating transcription that is originally possessed by the transcriptional factor (it may also be referred to as a transcriptional repression conversion peptide). Such "a functional peptide that converts an arbitrary transcriptional factor to a transcriptional repression factor" is not particularly limited, but is preferably a peptide comprising an amino acid sequence known as particularly a repressor domain sequence or an SRDX sequence. Such transcriptional repression conversion peptide is described in detail in JP Patent Publication (Kokai) No. 2005-204657 A and all peptides disclosed in this publication can be used herein.

Examples of the transcriptional repression conversion peptide include the peptides of the amino acid sequences represented by the following formulae (1) to (8), respectively.

$$\text{X1-Leu-Asp-Leu-X2-Leu-X3} \quad (1)$$

(wherein X1 denotes 0 to 10 amino acid residues, X2 denotes Asn or Glu, and X3 denotes at least 6 amino acid residues)

$$\text{Y1-Phe-Asp-Leu-Asn-Y2-Y3} \quad (2)$$

(wherein Y1 denotes 0 to 10 amino acid residues, Y2 denotes Phe or lie, and Y3 denotes at least 6 amino acid residues)

$$\text{Z1-Asp-Leu-Z2-Leu-Arg-Leu-Z3} \quad (3)$$

(wherein Z1 denotes Leu, Asp-Leu, or Leu-Asp-Leu. Z2 denotes Glu. Gln, or Asp, and Z3 denotes 0 to 10 amino acid residues)

$$\text{Asp-Leu-Z4-Leu-Arg-Leu} \quad (4)$$

(wherein Z4 denotes Glu. Gin, or Asp)

$$\text{alpha1-Leu-beta1-Leu-gamma1-Leu} \quad (5)$$

$$\text{alpha1-Leu-beta1-Leu-gamma2-Leu} \quad (6)$$

$$\text{alpha1-Leu-beta2-Leu-Arg-Leu} \quad (7)$$

$$\text{alpha2-Leu-beta1-Leu-Arg-Leu} \quad (8)$$

(and in the formulae (5) to (8), alpha1 denotes Asp, Asn. Glu, Gin, Thr, or Ser, alpha2 denotes Asn, Glu, Gln, Thr, or Ser, beta1 denotes Asp, Gln, Asn, Arg, Glu, Thr, Ser, or His, beta2 denotes Asn. Arg. Thr, Ser, or His, gamma1 denotes Arg, Gin, Asn. Thr, Ser, His, Lys, or Asp, and gamma2 denotes Gin, Asn, Thr, Ser, His, Lys, or Asp)

Transcriptional Repression Conversion Peptide of Formula (1)

In the transcriptional repression conversion peptide of the above formula (1), the number of amino acid residues denoted by X1 above may range from 0 to 10. Also, the specific types of amino acid composing the amino acid residues denoted by X1 are not particularly limited, and they may be of any type. The amino acid residues denoted by X1 are preferably as short as possible, in view of ease of synthesis of the transcriptional repression conversion peptide of formula (1). The number of amino acid residues that are specifically denoted by X1 is preferably 5 or less.

Similarly, in the case of the transcriptional repression conversion peptide of formula (1), the number of amino acid residues denoted by X3 above may be at least 6. Also, the specific types of amino acid composing amino acid residues denoted by X3 are not particularly limited, and they may be of any type.

Transcriptional Reoression Conversion Peotide of Formula (2)

In the transcriptional repression conversion peptide of formula (2) above, similarly to the case of X1 of the transcriptional repression conversion peptide of formula (1) above, the number of amino acid residues denoted by Y1 above may range from 0 to 10. Also, the specific types of amino acid composing the amino acid residues denoted by Y1 are not particularly limited, and they may be of any type. The specific number of amino acid residues denoted by Y is preferably 5 or less.

In the transcriptional repression conversion peptide of formula (2) above, similarly to the case of X3 of the transcriptional repression conversion peptide of formula (1) above, the number of amino acid residues denoted by Y3 above may be at least 6. Also, the specific types of amino acid composing the amino acid residues denoted by Y3 are not particularly limited, and they may be of any type.

Transcriptional Repression Conversion Peptide of Formula (3)

In the transcriptional repression conversion peptide of formula (3) above, the amino acid residues denoted by Z1 above includes 1 to 3 Leu residues. When the number of amino acids is 1, the amino acid is Leu. When the number of amino acids is 2, they are Asp-Leu. When the number of amino acids is 3, they are Leu-Asp-Leu.

Meanwhile, in the transcriptional repression conversion peptide of formula (3) above, the number of amino acid residues denoted by Z3 above may range from 0 to 10. Also, the specific types of amino acid composing amino acid residues denoted by Z3 are not particularly limited, and they may be of any type. Specifically, the number of amino acid residues denoted by Z3 is more preferably 5 or less. Specific examples of amino acid residues denoted by Z3 include, but are not limited to, Gly, Gly-Phe-Phe. Gly-Phe-Ala, Gly-Tyr-Tyr, and Ala-Ala-Ala.

Moreover, the total number of amino acid residues in the transcriptional repression conversion peptide represented by formula (3) is not particularly limited. In view of the ease upon synthesis, the number thereof is preferably 20 amino acids or less.

Transcriptional Repression Conversion Peptide of Formula (4)

The transcriptional repression conversion peptide of formula (4) is a hexamer (6 mer) consisting of 6 amino acid residues. In addition, when the amino acid residue denoted by Z4 in the transcriptional repression conversion peptide of formula (4) above is Glu, the amino acid sequence corresponds to a sequence ranging from amino acid 196 to amino acid 201 of *Arabidopsis thaliana* SUPERMAN protein (SUP protein).

Various transcriptional repression conversion peptides explained above can alter the properties of the above described transcriptional factor by fusion thereof to the transcriptional factor, so as to form a chimeric protein (fusion protein). Specifically, through fusion to the above described transcriptional factor so as to form a chimeric protein (fusion protein), such peptide can alter the relevant transcriptional factor to a transcriptional repression factor or a negative transcription coupling factor. Furthermore, such peptide can also convert a transcriptional repression factor that is not dominant to a dominant transcriptional repression factor.

A chimeric protein (fusion protein) can also be produced by obtaining a fusion gene using a polynucleotide encoding the above transcriptional repression conversion peptide and a gene encoding a transcriptional factor. Specifically, a fusion gene is constructed by linking a polynucleotide (referred to as transcriptional repression conversion polynucleotide) encoding the above transcriptional repression conversion peptide and a gene encoding the above transcriptional factor and then introduced into plant cells, so that a chimeric protein (fusion protein) can be produced by the cells. A specific example of the nucleotide sequence of the above transcriptional repression conversion polynucleotide is not particularly limited, as long as it is based on genetic codes and contains a nucleotide sequence corresponding to the amino acid sequence of the above transcriptional repression conversion peptide. Also, if necessary, the above transcriptional repression conversion polynucleotide may further contain a nucleotide sequence that serves as a joining site for linking with a transcriptional factor gene. Furthermore, when the amino acid reading frame of the above transcriptional repression conversion polynucleotide does not agree with the reading frame of a transcriptional factor gene, such polynucleotide may contain an additional nucleotide sequence for their agreement. Furthermore, such polynucleotide may also contain various additional polypeptides such as a polypeptide having a linker function for linking a transcriptional factor and a transcriptional repression conversion peptide and polypeptides (e.g., His, Myc, or Flag) for epitope labeling of the chimeric protein (fusion protein). Furthermore, the above chimeric protein (fusion protein) may contain structures other than polypeptides, if necessary, such as a sugar chain and an isoprenoid group.

A method for producing plant bodies is not particularly limited, as long as it comprises a process for production of the above-described chimeric protein of a transcriptional factor and a transcriptional repression conversion peptide in plant bodies. An example thereof is a production method comprising the steps of constructing an expression vector, transformation, selection, and the like. Each step is specifically explained as follows.

Step of Constructing Expression Vector

The step of constructing an expression vector is not particularly limited, as long as it is a step of constructing a recombinant expression vector containing a gene encoding the above transcriptional factor, a transcriptional repression conversion polynucleotide, and a promoter. As a vector to be used as a template for a recombinant expression vector, various conventionally known vectors can be used. For example, plasmids, phages, or cosmids can be used. A vector can be appropriately selected therefrom depending on a plant cell into which the vector is introduced or a method employed for introduction. Specific examples thereof include pBR322, pBR325, pUC 19, pUC 119, pBluescript, pBluescriptSK, and pBI vectors. Particularly, when a method for introducing a vector into a plant body is a method using *Agrobacterium*, a pBI binary vector is preferably used. Specific examples of such pBI binary vector include pBIG, pBIN 19, pBI101, pBI121, and pBI221.

A promoter to be used herein is not particularly limited, as long as it enables gene expression within a plant body. A known promoter can be preferably used. Examples of such promoter include a cauliflower mosaic virus 35S promoter (CaMV35S), various actin gene promoters, various ubiquitin gene promoters, a promoter of a nopaline synthase gene, a tobacco PR 1a gene promoter, a tomato ribulose 1,5-bisphosphate carboxylase oxidthse small subunit gene promoter, a napin gene promoter, and an oleosin gene promoter. Of these promoters, a cauliflower mosaic virus 35S promoter, actin gene promoters, or ubiquitin gene promoters can be more preferably used. The use of each of the above promoters enables strong expression of an arbitrary gene after its introduction into plant cells. A promoter is ligated to and introduced into a vector, so that a fusion gene can be expressed in which a gene encoding a transcriptional factor or a transcription coupling factor is linked to a transcriptional repression conversion polynucleotide. The specific structure of a recombinant expression vector is not particularly limited.

In addition, a recombinant expression vector may further contain other DNA segments in addition to a promoter and the above fusion gene. Examples of such other DNA segments are not particularly limited and include a terminator, a selection marker, an enhancer, and a nucleotide sequence for enhancing translation efficiency. Also, the above recombinant expression vector may further has a T-DNA region. A T-DNA region can enhance gene transfer efficiency particularly when the above recombinant expression vector is introduced into plant bodies using *Agrobacterium*.

A transcriptional terminator to be used herein is not particularly limited, as long as it has functions as a transcription termination site and may be a known transcriptional terminator. For example, specifically, a transcription termination region (Nos terminator) of a nopaline synthase gene, a transcription termination region (CaMV35S terminator) of cauliflower mosaic virus 35S, and the like can be preferably used. Of these examples, the Nos terminator can be more preferably used. In the above recombinant vector, a transcriptional terminator is placed at an appropriate position, so as to be able to prevent the occurrence of phenomena such as the synthesis of unnec-essarily long transcripts and reduced number of copies of a plasmid because of a strong promoter, after introduction into plant cells.

As a transformant selection marker, a drug resistance gene can be used, for example. A specific example of such drug resistance gene is a drug resistance gene against hygromycin, bleomycin, kanamycin, gentamicin, chloramphenicol, or the like. Hence, transformed plant bodies can be easily selected through selection of plant bodies that can grow in medium containing the above antibiotic.

An example of a nucleotide sequence for enhancing translation efficiency is a tobacco mosaic virus-derived omega sequence. The omega sequence is placed in the untranslated region (5' UTR) of a promoter, allowing the translation efficiency of the above fusion gene to be enhanced. As described above, the above recombinant expression vector can contain various DNA segments depending on purpose.

A method for constructing a recombinant expression vector is not particularly limited. The above promoter, a gene encoding a transcriptional factor, and a transcriptional repression conversion polynucleotide, as well as (if necessary) the above other DNA segments are introduced in a predetermined order into a vector appropriately selected as a template. For example, a fusion gene is constructed by linking a gene encoding a transcriptional factor and a transcriptional repression conversion polynucleotide. Next the fusion gene and a promoter (and if necessary, a transcriptional terminator and the like) are linked to construct an expression cassette and then the expression cassette is introduced into a vector.

Upon construction of a chimeric gene (fusion gene) and that of an expression cassette, for example, cleavage sites of DNA segments are treated to have protruding ends complementary from each other. Reaction is performed using a ligation enzyme, making it possible to determine the order of the DNA segments. In addition, when an expression cassette contains a terminator, from upstream, a promoter, the above chimeric gene, and a terminator should be placed in this order. Also, reagents for construction of a recombinant expression vector, that is, the types of restriction enzyme and ligation enzyme, for example, are also not particularly limited. Commercially available reagents may be appropriately selected and then used.

Moreover, a method for proliferating the above recombinant expression vector (production method) is also not particularly limited. Conventionally known methods can be used herein. In general, such vector may be proliferated within *Escherichia coli* as a host. At this time, a preferred type of *Escherichia coli* may be selected depending on the type of a vector.

Transformation Step

A transformation step that is performed in the present invention is a step of introducing the above fusion gene into plant cells using the above recombinant expression vector, so that the fusion gene is expressed. A method for introducing such gene into plant cells using a recombinant expression vector (transformation method) is not particularly limited. Any appropriate conventionally known method can be employed depending on plant cells. Specifically, for example, a method that uses *Agrobacterium* or a method that involves directly introducing such gene into plant cells can be employed herein. As such method that uses *Agrobacterium*, for example, a method described in Bechtold. E. Ellis, J. and Pelletier, G. (1993) In Planta *Agrobacterium*-mediated gene transfer by infiltration of adult *Arabidopsis* plants. C. R. Acad. Sci. Paris Sci. Vie, 316, 1194-1199, or a method described in Zyprian E, Kado Cl, *Agrobacterium*-mediated plant transformation by novel mini-T vectors in con-junction with a high-copy vir region helper plasmid. Plant Molecular Biology, 1990, 15(2), 245-256, can be employed.

As a method that involves direct introduction of DNA containing a recombinant expression vector and a target gene, into plant cells microinjection, electroporation, a polyethylene glycol method, a particle gun method, protoplast fusion, a calcium phosphate method, or the like can be employed.

Also, when a method that involves direct introduction of DNA into plant cells is employed. DNA to be used herein contains at least transcriptional units that are required for the expression of a target gene such as a promoter and a transcriptional terminator, and the target gene. Vector functions are not essential herein. Furthermore, even if DNA contains only the protein coding region of a target gene having no transcriptional unit, such DNA can also be used herein, as long as it can be integrated into a host transcriptional unit and the target gene can be expressed.

Examples of plant cells, into which DNA containing the above recombinant expression vector and a target gene or DNA containing only target gene DNA without containing any expression vector is introduced, include cells of each tissue in plant organs such as flowers, leaves, and roots, calli, and suspension-cultured cells. In a method for producing the plant body according to the present invention, as the above recombinant expression vector, an appropriate vector may be adequately constructed depending on the type of a plant body to be produced. Alternatively, a versatile recombinant expression vector is constructed in advance and then the vector may be introduced into plant cells. Specifically, the method for producing the plant body according to the present invention may or may not comprise a step of constructing DNA for transformation using the above recombinant expression vector.

Other Steps and Methods

A method for producing the plant body according to the present invention comprises at least the above transformation step. Furthermore, the method may also comprise a step of constructing DNA for transformation using the above recombinant expression vector and may further comprise other steps. Specifically, an example of such steps is a selection step of selecting an appropriate transformant from transformed plant bodies.

A selection method is not particularly limited. For example, selection can be carried out based on drug resistance such as hygromycin resistance. Selection can also be carried out based on dry weights of plant bodies themselves or dry weights of arbitrary organs or tissues after transformants are grown. For example, an example of a selection method based on dry weights is a method that involves collecting the above-ground parts of plant bodies, performing dry treatment under predetermined conditions, measuring the weights, and then comparing the weights with the dry weights of the above-ground parts of untransformed plant bodies (see Examples described later).

In the method for producing the plant body according to the present invention, the above fusion gene is introduced into plant bodxies, so as to make it possible to obtain, from the plant bodies, progeny with significantly improved fat and oil contents through sexual reproduction or asexual reproduction. Also, it becomes possible to obtain, from the plant bodies or the progeny thereof, plant cells and propagation materials such as seeds, fruits, stocks, calli, tubers, cuttings, and masses so as to mass-produce the plant bodies based on them. Therefore, the method for producing the plant body according to the present invention may comprise a propagation step (mass-production step) for propagation of plant bodies after selection.

In addition, examples of the plant body of the present invention include at least any one of grown individual plants, plant cells, plant tissues, calli, and seeds. Specifically, in the present invention, they are all regarded as plant bodies, as long as they are in a state such that they can be finally grown to individual plants. Also, examples of the above plant cells include plant cells of various forms. Examples of such plant cells include suspension-cultured cells, protoplasts, and leaf sections. Plant bodies can be obtained by growing and causing differentiation of these plant cells. In addition, re-generation of plant bodies from plant cells can be carried out by a conventionally known method depending on the type of plant cell. Therefore, the method for producing the plant body according to the present invention may comprise a re-generation step for regenerating plant bodies from plant cells or the like.

Also, the method for producing the plant body according to the present invention is not limited to a method that involves transformation using a recombinant expression vector, and other methods may also be employed. Specifically, for example, the above chimeric protein (fusion protein) may be directly administered to plant bodies. In this case, a chimeric protein (fusion protein) is administered to plant bodies in their early life, so that fat and oil contents can be improved at sites of plant bodies that are finally used. Moreover, a method for administration of a chimeric protein (fusion protein) is also not particularly limited, and various known methods may be employed for such purpose.

As explained above, according to the present invention, through expression of a chimeric protein of a predetermined transcriptional factor and the above functional peptide, plant bodies can be provided, wherein plant weights (that is, biomass levels) are improved and substance productivity per individual plant is changed (improved or decreased) compared with that of wild-type plant bodies. When the above chimeric protein is expressed by plant bodies, the activity for accelerating transcription of a target transcriptional factor may be suppressed or transcriptional repression effects may be exerted on the homologous sequence of a cis sequence that is recognized by the target transcriptional factor. Furthermore, the chimeric protein may act to alter the affinity specificity of another factor, DNA, RNA, lipid, or carbohydrate that has affinity for the target transcriptional factor or transcription coupling factor. Alternatively, the chimeric protein may act to improve the affinity of a substance that has no affinity for the target transcriptional factor. In the plant body according to the present invention, a target transcriptional factor of a chimeric protein, a transcriptional factor that recognizes a cis sequence having homology with a cis sequence to be recognized by the target transcriptional factor, a transcriptional factor having homology with the target transcriptional factor of the chimeric protein, other factors having affinity for the target transcriptional factor of the chimeric protein, and the like are similarly expressed. However, gene expression to be controlled can be suppressed dominant-negatively because of the above-described action and effects of the chimeric protein. Accordingly, it is thought that in the plant body according to the present invention, the expression level of a gene group involved in plant growth as well as the expression level of a gene group involved in fat and oil production and/or decomposition of the produced fats and oils are changed, as a result, the biomass levels are significantly improved and fat and oil contents are significantly changed.

Here, the expression, "fat and oil contents are significantly changed" refers to a case in which fat and oil levels are improved although the seed mass per grain remains unchanged compared with that of wild-type plants; a case in which fat and oil levels are improved while the seed mass per grain is significantly increased or decreased compared with that of wild-type plants; or a case in which fat and oil contents in seeds are improved or decreased compared with those of wild-type plants. In any case, the level of fats and oils produced by an individual plant is changed.

More specifically, when a chimeric protein of the transcriptional factor At3g04070 or the transcriptional factor At1g18330 is expressed, the biomass level in the plant body is increased, but the fat and oil content is decreased. In contrast, when a chimeric protein of the transcriptional factor At3g45150 is expressed, both the biomass level and the fat and oil content are increased.

Among examples of the plant body according to the present invention, plant bodies in which fat and oil contents are increased can be used for a method for producing plant-derived fats and oils. For example, fats and oils can be produced by growing the plant body according to the present invention, harvesting seeds, and then collecting fat and oil components from the harvested seeds. Particularly, a method for producing fats and oils using the plant body according to the present invention can be said to be excellent in productivity because the fat and oil content of the thus produced individual plant is high. That is to say, if it is assumed that the number of cultivated plants per unit of cultivated area stays constant, the fat and oil level produced per unit of cultivated area can be significantly improved through the use of the plant body according to the present invention. Therefore, the use of the plant body according to the present invention makes it possible to significantly reduce the production costs of fats and oils.

Furthermore, a method for producing fats and oils using the plant body according to the present invention can be said to be excellent in prodxluctivity because of resulting high fat and oil contents in seeds per unit of weight.

In addition, examples of fats and oils to be produced by the method for producing fats and oils using the plant body according to the present invention are not particularly limited and include plant-derived fats and oils such as soybean oil, sesame oil, olive oil, coconut oil, rice oil, cottonseed oil, sunflower oil, corn oil, safflower oil, and rapeseed oil. Moreover, the thus produced fats and oils can be broadly used for household and industrial applications. The fats and oils can further be used as raw materials for biodiesel fuel. Specifically, through the use of plant bodies according to the present invention, the above-mentioned fats and oils for household or industrial applications, biodiesel fuel, or the like can be produced at low cost.

In addition, among examples of the plant body according to the present invention, plant bodies with decreased fat and oil contents can be used for a method for producing bioalcohol using lignocellulose contained in plants. Specifically, hioalcohol with excellent glycosylation efficiency and low impurity content can be produced due to the low levels of fat and oil components (which are impurities) in the step of glycosylating lignocellulose.

EXAMPLES

The present invention will be described in detail using examples as follows, but the technical scope of the present invention is not limited by these examples.

Example 1

Amplification of Transcriptional Factor Gene

A DNA fragment of the coding region of transcriptional factor At3g04070 excluding the termination codon was amplified by PCR using primers described below from an *Arabidopsis thaliana* cDNA library. PCR was performed in 25 cycles each consisting of 94 degrees C. for 1 minute, 47 degrees C. for 2 minutes and an extension reaction at 74 degrees C. for 1 minute. Next, PCR products were separated and collected by agarose gel electrophoresis.

```
Forward primer 1
GATGATAAGCAAGGATCCAAGATCGAGTTT   (SEQ ID NO: 7)

Reverse primer 1
GCCTTGATATTGAAGGTGAGAACTCATCAT   (SEQ ID NO: 8)
```

Preparation of Modified Transcriptional Factor

A p35SSXG vector having an Sma I site and a repressor domain (amino acid sequence: GLDLDLIELRLGFA (SEQ ID NO: 9)) sequence downstream of a CaMV35S prnmoter was used to add a repressor domain sequence to the 3' end of the transcriptional factor gene encoded by the DNA fragment. To link the transcriptional factor gene sequence and the repressor domain sequence, the vector was digested with Sma I and then the PCR amplified fragment encoding the above transcriptional factor was inserted. Thus, p35SSXG (At3g04070) was prepared.

Construction of Modified Transcriptional Factor Expression Vector

For gene transfer into plants using Agrobacterium, pBCKH was used as a binary vector. This vector was constructed by incorporating a Gateway vector conversion system cassette (Invitrogen) into the Hind III site of pBIG (Hygr) (Nucleic Acids Res. 18, 203 (1990)). To incorporate the modified transcriptional factor gene sequence into the vector, the vector and p35SSXG (At3g04070) were mixed and then a recombination reaction was carried out using GATEWAY LR clonase (Invitrogen). Thus, pBCKH-p35SSXG (At3g04070) was constructed.

Introduction of Modified Transcriptional Factor Gene Expression Vector into Plant Arabidopsis thaliana (Columbia (Col-0)) was used as a plant for introduction of the modified transcriptional factor. Gene transfer was carried out according to Transformation of Arabidopsis thaliana by Vacuum Infiltration (http://www.bch.msu.edu/pamgreen/protocol.htm). However, plants were only infected by immersing them in an Agrobacterium solution without performing decompression treatment. Specifically, the modified transcriptional factor expression vector pBCKH-p35SSXG (At3g04070) was introduced into soil bacterium Agrobacterium tumefaciens strain GV3101 (C58C1Rifr) pMP90 (Gmr) (koncz and Schell 1986) strain by electroporation. The thus introduced bacteria were cultured in 1 liter of YEP medium containing an antibiotic (kanamycin (Km): 50 microgram/ml; gentamicin (Gm); 25 microgram/ml: rifampicin (Rif): 50 microgram/ml) until OD600 reached 1. Sub-sequently, bacteria were collected from the culture solution and then suspended in 1 liter of medium for infection (infiltration medium containing 2.2 g of MS salt, 1× B5 vitamins, 50 g of sucrose, 0.5 g of MES, 0.044 micro M benzylaminopurine, and 400 microliter of Silwet per liter, pH 5.7).

Arabidopsis thaliana plants grown for 14 days were immersed in the solution for 1 minute for infection. After infection, cultivation was continued to fructification. Harvested seeds (T1 seeds) were sterilized in 50% bleach with 0.02% Triton X-100 solution for 7 minutes, rinsed 3 times with sterile water, and then germinated on a sterilized hygromycin selective medium (4.3 g/l MS salts, 0.5% sucrose, 0.5 g/l MES, pH 5.7, 0.8% agar, 30 mg/l hygromycin, and 250 mg/l Vancomycin). Ten (10) lines of transformed plant bodies (T1 plants) that had grown on the above hygromycin selective medium were selected per modified transcription gene. Plants were then transplanted into pots with a diameter of 50 mm containing vermiculite mixed with soil. They were cultivated at 22 degrees C. under 16-hour-light/8-hour-dark photoperiods and light intensity ranging from approximately 60 to 80 micro mol m$^{-2}$s$^{-1}$. Thus, seeds (T2 seeds) were obtained.

Analysis of T2 Seed

Ten (10) lines into which At3g04070-SRDX had been introduced were each analyzed. Fat and oil contents were measured for T1 generation plants and T2 seeds.

Quantitative analysis of fats and oils was conducted using MARAN-23 (Resonance Instruments Ltd., UK) H-NMR and analysis software RI-NMR Ver. 2.0, so that 2 mg to 10 mg of Arabidopsis thaliana seeds were measured. A calibration curve was produced using olive oil as a standard substance for fats and oils. Thus, fat and oil contents (% by weight) in seeds were found.

The results of analyzing T2 seeds of the 10 lines produced for the At3g04070-SRDX gene are summarized in Table 1. The seed fat and oil content of control WT into which no gene had been introduced was 34.9+/−3.8%. The fat and oil contents of lines into which the modified transcriptional factor gene had been introduced were 19.5% at minimum and 29.4% at maximum.

TABLE 1

| Line name | Fat and oil content |
| --- | --- |
| At3g04070SRDX-1 | 19.5% |
| At3g04070SRDX-2 | 19.9% |
| At3g04070SRDX-3 | 23.3% |
| At3g04070SRDX-4 | 27.4% |
| At3g04070SRDX-5 | 26.8% |
| At3g04070SRDX-6 | 28.0% |
| At3g04070SRDX-7 | 28.6% |
| At3g04070SRDX-8 | 29.4% |
| At3g04070SRDX-9 | 25.5% |
| At3g04070SRDX-10 | 24.1% |
| WT (n = 34) | 34.9 ± 3.8% |

Analysis of Biomass

T2 seeds of 2 lines out of 10 lines into which the At3g04070-SRDX gene had been introduced were germinated and then cultivated. The biomass level per individual plant was measured.

First, T2 plants were cultivated for analysis of T3 plant bodies. T2 seeds were sterilized in 50% bleach with 0.02% Triton X-100 solution for 7 minutes, rinsed 3 times with sterile water, and then germinated on sterilized medium for germination (4.3 g/l MS salts, 0.5% sucrose, pH 5.7, 0.8% agar, and 10 mg/l hygromycin). Three (3) weeks after germination, the thus grown individual plants into which the gene had been introduced (specifically, 5 to 6 transformed plant bodies (T2 plants) per line) were transplanted into pots with a diameter of 50 mm containing vermiculite mixed with soil. As control plants, four non-recombinant Arabidopsis thaliana plants were transplanted. They were further cultivated at 22 degrees C. under 16-hour-light/8-hour-dark photoperiods and light intensity ranging from approximately 30 to 45 micro mol m$^{-2}$s$^{-1}$ for 11 weeks.

Above-the-ground plant bodies were put into paper bags and then dried under conditions of 22 degrees C. and humidity of 60% for 2 weeks. Total biomass weight levels were then determined. The results are shown in Table 2.

TABLE 2

| Sample name | Biomass weight Biomass weight (mg) | Percentage increase in biomass |
| --- | --- | --- |
| At3g04070SRDX-1-1 | 915.5 | 4.0% |
| At3g04070SRDX-1-2 | 978.6 | 11.1% |
| At3g04070SRDX-1-3 | 936.2 | 6.3% |
| At3g04070SRDX-1-4 | 1048.0 | 19.0% |
| At3g04070SRDX-1-5 | 910.0 | 3.3% |
| At3g04070SRDX-1-6 | 946.9 | 7.5% |
| average | 955.9 | 8.6% |
| At3g04070SRDX-2-1 | 1019.7 | 15.8% |
| At3g04070SRDX-2-2 | 1037.2 | 17.8% |

TABLE 2-continued

| Sample name | Biomass weight Biomass weight (mg) | Percentage increase in biomass |
|---|---|---|
| At3g04070SRDX-2-3 | 1016.6 | 15.4% |
| At3g04070SRDX-2-4 | 987.7 | 12.2% |
| At3g04070SRDX-2-5 | 1027.2 | 16.6% |
| average | 1017.7 | 15.6% |
| WT1 | 903.4 | — |
| WT2 | 880.3 | — |
| WT3 | 911.1 | — |
| WT4 | 827.6 | — |
| average | 880.6 | — |

As a result, the biomass level per individual plant of the line into which the At3g04070-SRDX gene had been introduced was increased by 19% at maximum compared with that of the wild-type plants. Also, the biomass levels of the two lines were increased by 8.6% and 15.6%, respectively, on average. Hence, the biomass production per individual plant could be increased through introduction of the above modified transcriptional factor gene At3g04070-SRDX into which the repressor domain had been added. In addition, regarding At3g04070, functions relating to biomass have never before been reported.

Example 2

Amplification of Transcriptional Factor Gene

A DNA fragment of the coding region of transcriptional factor At1g18330 excluding the termination codon was amplified by PCR using primers described below from *Arabidopsis thaliana* cDNA library. PCR was performed in 25 cycles each consisting of 94 degrees C. for 1 minute, 47 degrees C. for 2 minutes, and an extension reaction at 74 degrees C. for 1 minute. Next, PCR products were separated and collected by agarose gel electrophoresis.

```
Forward primer 1
GATGGCCGCTGAGGATCGAAGTGAGGAACT  (SEQ ID NO: 10)

Reverse primer 1
GCATATACGTGCTCTTTGGCTTTTCTTTTC  (SEQ ID NO: 11)
```

Preparation of Modified Transcriptional Factor

A p35SSXG vector having an Sma I site and a repressor domain (amino acid sequence: GLDLDLELRLGFA (SEQ ID NO: 9)) sequence downstream of a CaMV35S promoter was used to add a repressor domain sequence to the 3' end of the transcriptional factor gene encoded by the DNA fragment. To link the transcriptional factor gene sequence and the repressor domain sequence, the vector was digested with Sma I and then the PCR amplified fragment encoding the above transcriptional factor was inserted. Thus, p35SSXG (At1g18330) was prepared.

Construction of Modified Transcriptional Factor Expression Vector

For gene transfer using *Agrobacterium* into plants, pBCKH was used as a binary vector. This vector was constructed by incorporating a cassette of a Gateway vector conversion system (Invitrogen) into a Hind III site of pBIG (Hygr) (Nucleic Acids Res. 18, 203 (1990)). To incorporate the modified transcriptional factor gene sequence into the vector, the vector and p35SSXG (At1g18330) were mixed and then a recombination reaction was carried out using GATEWAY LR clonase (Invitrogen). Thus, pBCKHI-p35SSXG (At1g 8330) was constructed.

Introduction of Modified Transcriptional Factor Gene Expression Vector into Plant

*Arabidopsis thaliana* (Columbia (Col-0)) was used as a plant for introduction of the modified transcriptional factor. Gene transfer was carried out according to Transformation of *Arabidopsis thaliana* by Vacuum Infiltration (http://www.bch.msu.edu/pamgreen/protocol.htm). However, plants were only infected by immersing them in an *Agrobacterium* solution without performing decompression treatment. Specifically, the modified transcriptional factor expression vector pBCKH-p35SSXG (At1g18330) was introduced into soil bacterium *Agrobacterium tumefaciens* strain GV3101 (C58C1Rifr) pMP90 (Gmr) (koncz and Schell 1986) strain by electroporation. The thus introduced bacteria were cultured in 1 liter of YEP medium containing an antibiotic (kanamycin (Km) 50 microgram/ml, gentamicin (Gm) 25 microgram/ml, and rifampicin (Rif) 50 microgram/ml) until OD600 reached 1. Sub-sequently, bacteria were collected from the culture solution and then suspended in 1 liter of medium for infection (Infiltration medium containing 2.2 g of MS salt, 1× B5 vitamins, 50 g of sucrose, 0.5 g of MES, 0.044 micro M benzylaminopurine, and 400 microliter of Silwet per liter, pH5.7).

*Arabidopsis thaliana* plants grown for 14 days were immersed in the solution for 1 minute for infection. After infection, cultivation was continued to fructification. Harvested seeds (T1 seeds) were sterilized in 50% bleach with 0.02% Triton X-100 solution for 7 minutes, rinsed 3 times with sterile water, and then germinated on sterilized hygromycin selective medium (4.3 g/l MS salts, 0.5% sucrose, 0.5 g/l MES, pH 5.7, 0.8% agar, 30 mg/l hygromycin, and 250 mg/l Vancomycin). Ten (10) lines of transformed plant bodies (T1 plants) that had grown on the above hygromycin selective medium were selected per modified transcription gene. Plants were then transplanted into pots with a diameter of 50 mm containing vermiculite mixed with soil. They were cultivated at 22 degrees C. under 16-hour-light/8-hour-dark photoperiods and light intensity ranging from approximately 60 to 80 micro mol $m^{-2}s^{-1}$. Thus, seeds (T2 seeds) were obtained.

Analysis of T2 Seed

Ten (10) lines into which At1g18330-SRDX had been introduced were each analyzed. Fat and oil contents were measured for T1 generation plants and T2 seeds. Quantitative analysis of fats and oils was conducted using MARAN-23 (Resonance Instruments Ltd., UK) H-NMR and analysis software RI-NMR Ver. 2.0, so that 2 mg to 10 mg of *Arabidopsis thaliana* seeds were measured. A calibration curve was produced using olive oil as a standard substance for fats and oils. Thus, fat and oil contents (% by weight) in seeds were found.

The results of analyzing T2 seeds of the 10 lines produced for the At1g18330-SRDX gene are summarized in Table 3. The seed fat and oil content of control WT into which no gene had been introduced was 34.9+/−3.8%. The fat and oil contents of lines into which the modified transcriptional factor gene had been introduced were 22.0% at minimum and 33.7% at maximum.

TABLE 3

| Gene name | Lipid level | Percentage decrease |
|---|---|---|
| At1g18330-1 | 33.7% | −3.6% |
| At1g18330-2 | 30.2% | −13.5% |
| At1g18330-3 | 30.6% | −12.3% |

TABLE 3-continued

| Gene name | Lipid level | Percentage decrease |
|---|---|---|
| At1g18330-4 | 24.7% | −29.3% |
| At1g18330-5 | 26.2% | −24.9% |
| At1g18330-6 | 26.5% | −24.2% |
| At1g18330-7 | 22.8% | −34.6% |
| At1g18330-8 | 22.0% | −37.0% |
| At1g18330-9 | 26.9% | −23.0% |
| At1g18330-10 | 32.8% | −5.9% |
| WT (n = 34) | 34.9 ± 3.8% | |

Analysis of Biomass

T2 seeds of 1 line out of the 10 lines into which the At1g18330-SRDX gene had been introduced were germinated and then cultivated. The biomass level per individual plant was measured. First, T2 plants were cultivated for analysis of T3 plant bodies. T2 seeds were sterilized in 50% bleach with 0.02% Triton X-100 solution for 7 minutes, rinsed 3 times with sterile water, and then germinated on sterilized medium for germination (4.3 g/l MS salts, 0.5% sucrose, pH 5.7, 0.8% agar, and 10 mg/l hygromycin). Three (3) weeks after germination, the thus grown individual plants into which the gene had been introduced (specifically, 4 transformed plant bodies (T2 plants)) were transplanted into pots with a diameter of 50 mm containing vermiculite mixed with soil. As control plants, four non-recombinant *Arabidopsis thaliana* plants were transplanted. They were further cultivated at 22 degrees C. under 16-hour-light/8-hour-dark photoperiods and light intensity ranging from approximately 30 to 45 micro mol $m^{-2}s^{-1}$ for 11 weeks.

Above-the-ground plant bodies were put into paper bags and then dried under conditions of 22 degrees C. and humidity of 60% for 2 weeks. Total biomass weight levels were then determined. The results are shown in Table 4.

TABLE 4

| Sample name | Biomass weight (mg) | Percentage increase in biomass |
|---|---|---|
| At1g18330SRDX-5-1 | 978.8 | 13.9% |
| At1g18330SRDX-5-2 | 1202.5 | 39.9% |
| At1g18330SRDX-5-3 | 1015.9 | 18.2% |
| At1g18330SRDX-5-4 | 884.8 | 3.0% |
| average | 1020.5 | 18.8% |
| WT1 | 698.0 | — |
| WT2 | 958.6 | — |
| WT3 | 884.1 | — |
| WT4 | 896.2 | — |
| average | 859.2 | — |

As a result, the biomass level per individual plant of the line into which the At1g18330-SRDX gene had been introduced was increased by 39.9% at maximum compared with that of the wild-type plants. Also, the biomass level per individual plant of each line was increased by 18.8%, on average. Hence, the biomass production per individual plant could be increased through introduction of the above modified transcriptional factor gene At1g18330-SRDX into which the repressor domain had been added. In addition, regarding At1g18330, there is a report that flowering is delayed by functional deficiency, but there is no report that it relates to biomass.

Example 3

Amplification of Transcriptional Factor Rene

A DNA fragment of the coding region of transcriptional factor At3g45150 excluding the termination codon was amplified by PCR using primers described below from *Arabidopsis thaliana* cDNA library. PCR was performed in 25 cycles each consisting of 94 degrees C. for 1 minute, 47 degrees C. for 2 minutes, and an extension reaction at 74 degrees C. for 1 minute. Next, PCR products were separated and collected by agarose gel electrophoresis.

```
Forward primer 1
ATGGATTCGAAAAATGGAATTAAC    (SEQ ID NO: 12)

Reverse primer 1
AACTGTGGTTGTGGCTGTTGTTG     (SEQ ID NO: 13)
```

Preparation of Modified Transcriptional Factor

A p35SSXG vector having an Sma I site and a repressor domain (amino acid sequence: GLDLDLELRLGFA (SEQ ID NO: 9)) sequence downstream of a CaMV35S promoter was used to add a repressor domain sequence to the 3' end of the transcriptional factor gene encoded by the DNA fragment. To link the transcriptional factor gene sequence and the repressor domain sequence, the vector was digested with Sma I and then the PCR amplified fragment encoding the above transcriptional factor was inserted. Thus, p35SSXG (At3g45150) was prepared.

Construction of Modified Transcriptional Factor Expression Vector

For gene transfer using *Agrobacterium* into plants, pBCKH was used as a binary vector. This vector was constructed by incorporating a cassette of a Gateway vector conversion system (Invitrogen) into a Hind III site of pBIG (Hygr) (Nucleic Acids Res. 18, 203 (1990)). To incorporate the modified transcriptional factor gene sequence into the vector, the vector and p35SSXG (At3g45150) were mixed and then a recombination reaction was carried out using GATEWAY LR clonase (Invitrogen). Thus, pBCKH-p35SSXG (At3g45150) was constructed.

Introduction of Modified Transcriptional Factor Gene Expression Vector into Plant

*Arabidopsis thaliana* (Columbia (Col-0)) was used as a plant for introduction of the modified transcriptional factor. Gene transfer was carried out according to Transformation of *Arabidopsis thaliana* by Vacuum Infiltration (http://www.bch.msu.edu/pamgreen/protocol.htm). However, plants were only infected by immersing them in an *Agrobacterium* solution without performing decompression treatment. Specifically, the modified transcriptional factor expression vector pBCKIH-p35SSXG (At3g45150) was introduced into soil bacterium *Agrobacterium tumefaciens* strain GV3101 (C58C1Rifr) pMP90 (Gmr) (koncz and Schell 1986) strain by electroporation. The thus introduced bacteria were cultured in 1 liter of YEP medium containing an antibiotic (kanamycin (Km) 50 microgram/ml, gentamicin (Gm) 25 microgram/ml, and rifampicin (Rif) 50 microgram/ml) until OD600 reached 1. Sub-sequently, bacteria were collected from the culture solution and then suspended in 1 liter of medium for infection (Infiltration medium containing 2.2 g of MS salt, 1× B5 vitamins, 50 g of sucrose, 0.5 g of MES, 0.044 micro M benzylaminopurine, and 400 microliter of Silwet per liter, pH5.7).

*Arabidopsis thaliana* plants grown for 14 days were immersed in the solution for 1 minute for infection. After infection, cultivation was continued to fructification.

Harvested seeds (T1 seeds) were sterilized in 50% bleach with 0.02% Triton X-100 solution for 7 minutes, rinsed 3 times with sterile water, and then germinated on sterilized hygromycin selective medium (4.3 g/l MS salts, 0.5% sucrose, 0.5 g/l MES, pH 5.7, 0.8% agar, 30 mg/l hygromycin, and 250 mg/l Vancomycin). Ten (10) lines of transformed plant bodies (T1 plants) that had grown on the above hygromycin selective medium were selected per modified transcription gene. Plants were then transplanted into pots with a diameter of 50 mm containing vermiculite mixed with soil. They were cultivated at 22 degrees C. under 16-hour-light/8-hour-dark photoperiods and light intensity ranging from approximately 60 to 80 micro mol $m^{-2}s^{-1}$. Thus, seeds (T2 seeds) were obtained.

Analysis of Fat and Oil Content in T2 Seed

Ten (10) lines into which At3g45150-SRDX had been introduced were each analyzed. Fat and oil contents were measured for T1 generation plants and T2 seeds. Quantitative analysis of fats and oils was conducted using MARAN-23 (Resonance Instruments Ltd., UK) H-NMR and analysis software RI-NMR Ver. 2.0, so that 2 mg to 10 mg of *Arabidopsis thaliana* seeds were measured. A calibration curve was produced using olive oil as a standard substance for fats and oils. Thus, fat and oil contents (% by weight) in seeds were found.

As a result of analyzing T2 seeds of the 10 lines produced for the At3g45150-SRDX gene, the fat and oil contents in T2 seeds of the 10 lines were 46.4%, 40.7%, 40.0%, 35.7%, 35.4%, 34.8%, 33.6%, 31.1%, 30.6%, and 26.7% (46.4% at maximum and 26.7% at minimum). The seed fat and oil content of control WT into which no gene had been introduced was 34.9+/−3.8%. From these lines, the line with the fat and oil content of 40.7% was used for the subsequent experiments.

Cultivation Test and Analysis of Biomass and Fat and Oil Content

T2 seeds of 1 line out of the 10 lines into which the At3g45150-SRDX gene had been introduced were germinated and then cultivated. The biomass level per individual plant was measured. First, T2 plants were cultivated for analysis of T3 plant bodies. T2 seeds were sterilized in 50% bleach with 0.02% Triton X-100 solution for 7 minutes, rinsed 3 times with sterile water, and then germinated on sterilized medium for germination (4.3 g/l MS salts, 0.5% sucrose, pH 5.7, 0.8% agar, and 10 mg/l hygromycin). Three (3) weeks after germination, the thus grown individual plants into which the gene had been introduced (specifically, 5 transformed plant bodies (T2 plants)) were transplanted into pots with a diameter of 50 mm containing vermiculite mixed with soil. As control plants, four non-recombinant *Arabidopsis thaliana* plants were transplanted. They were further cultivated at 22 degrees C. under 16-hour-light/8-hour-dark photoperiods and light intensity ranging from approximately 30 to 45 micro mol $m^{-2}s^{-1}$ for 11 weeks.

Above-the-ground plant bodies were put into paper bags and then dried under conditions of 22 degrees C. and humidity of 60% for 2 weeks. Total biomass weight levels were then determined and the above fat and oil contents were measured. The results are shown in Table 5.

TABLE 5

| Sample name | Biomass weight (mg) | Percentage increase in biomass | Fat and oil content in seed | Percentage increase in fats and oils |
|---|---|---|---|---|
| At3g45150SRDX-27-1 | 893.7 | 25.9% | 36.0% | 3.1% |
| At3g45150SRDX-27-2 | 875.3 | 23.3% | 36.6% | 4.9% |
| At3g45150SRDX-27-3 | 1115.7 | 57.2% | 37.1% | 6.5% |
| At3g45150SRDX-27-5 | 820.1 | 15.6% | 35.1% | 0.7% |
| At3g45150SRDX-27-6 | 827.7 | 16.6% | 35.9% | 3.0% |
| average | 906.5 | 27.7% | 36.1% | 3.7% |
| WT1 | 818.7 | — | 35.3% | — |
| WT2 | 784.5 | — | 34.8% | — |
| WT3 | 627.5 | — | 35.2% | — |
| WT4 | 608.0 | — | 34.1% | — |
| average | 709.6 | — | 34.9% | — |

As a result, the biomass level per individual plant of the line into which the At3g45150-SRDX gene had been introduced was increased by 57.2% at maximum compared with that of the wild-type plants. The biomass level per individual plant of each line was increased by 27.7% on average. Also, when the fat and oil contents in dry seeds were measured by pulse NMR, they were confirmed to be improved by 6.5% at maximum and 3.7% on average. Hence, the biomass production per individual plant could be increased through introduction of the above modified transcriptional factor gene At3g45150-SRDX into which the repressor domain had been added. In addition, regarding At3g45150, there is a report that functional deficiency induces underde-velopment of pollens, but there is no report that this matter relates to biomass.

The invention claimed is:

1. A method for producing a plant exhibiting an improved biomass level and having an improved productivity of a substance per individual plant compared with a wild type plant, comprising the steps of:
introducing a fusion gene into a plant, wherein the fusion gene codes for a chimeric protein comprising a transcriptional factor comprising any one of the following proteins (a) to (b) and a functional peptide that converts an arbitrary transcriptional factor into a transcriptional repression factor:
(a) a protein comprising the amino acid sequence shown in SEQ ID NO: 6; and
(b) a protein comprising the amino acid sequence of SEQ ID NO: 6 but with 1-20 amino acid changes, wherein said amino acid changes are selected from the group consisting of a deletion, a substitution, an addition, and an insertion, and wherein the protein has an activity of accelerating transcription, and
selecting a plant having the introduced fusion gene, exhibiting an improved biomass level and having an improved productivity of a substance compared with a wild type plant.

2. The method according to claim 1, wherein the activity of accelerating transcription of the transcriptional factor is suppressed.

3. The method according to claim 1, wherein the chimeric protein has transcriptional repression factor activity.

4. The method according to claim 1, wherein the functional peptide has the amino acid sequence represented by any one of the following formulae (1) to (8):

$$X1\text{-Leu-Asp-Leu-}X2\text{-Leu-}X3 \text{ (SEQ ID NO: 14 with deletion of 0-10 residues from the N-terminus)} \quad (1)$$

(wherein X1 denotes 0 to 10 amino acid residues, X2 denotes Asn or Glu, and X3 denotes at least 6 amino acid residues);

$$Y1\text{-Phe-Asp-Leu-Asn-}Y2\text{-}Y3 \text{ (SEQ ID NO: 15 with deletion of 0-10 residues from the N-terminus)} \quad (2)$$

(wherein Y1 denotes 0 to 10 amino acid residues, Y2 denotes Phe or Ile, and Y3 denotes at least 6 amino acid residues);

$$Z1\text{-Asp-Leu-}Z2\text{-Leu-Arg-Leu-}Z3 \text{ (SEQ ID NO: 16 with deletion of 0-10 residues from the C-terminus and deletion of 0-2 residues from the N-terminus)} \quad (3)$$

(wherein Z1 denotes Leu, Asp-Leu, or Leu-Asp-Leu, Z2 denotes Glu, Gln, or Asp, and Z3 denotes 0 to 10 amino acid residues);

$$\text{Asp-Leu-}Z4\text{-Leu-Arg-Leu (SEQ ID NO: 17)} \quad (4)$$

(wherein Z4 denotes Glu, Gln, or Asp);

$$\alpha1\text{-Leu-}\beta1\text{-Leu-}\gamma1\text{-Leu (SEQ ID NO: 18);} \quad (5)$$

$$\alpha1\text{-Leu-}\beta1\text{-Leu-}\gamma2\text{-Leu (SEQ ID NO: 19);} \quad (6)$$

$$\alpha1\text{-Leu-}\beta1\text{-Leu-Arg-Leu (SEQ ID NO: 20); and} \quad (7)$$

$$\alpha2\text{-Leu- }\beta1\text{-Leu-Arg-Leu (SEQ ID NO: 21)} \quad (8)$$

(and in the formulae (5) to (8), $\alpha1$ denotes Asp, Asn, Glu, Gln, Thr, or Ser, $\alpha2$ denotes Asn, Glu, Gln, Thr, or Ser, $\beta1$ denotes Asp, Gln, Asn, Arg, Glu, Thr, Ser, or His, $\beta2$ denotes Asn, Arg, Thr, Ser, or His, $\gamma1$ denotes Arg, Gln, Asn, Thr, Ser, His, Lys, or Asp, and $\gamma2$ denotes Gln, Asn, Thr, Ser, His, Lys, or Asp).

5. The method according to claim 1, wherein the plant weight is significantly improved.

6. The method according to claim 1, wherein the substance productivity per individual plant is productivity of fats and oils contained in seeds.

7. The method according to claim 1, wherein the plant is an angiosperm.

8. The method according to claim 1, wherein the plant is a dicotyledon.

9. The method according to claim 1, wherein the plant is a plant of the family Brassicaceae.

10. The method according to claim 1, wherein the plant is *Arabidopsis thaliana*.

\* \* \* \* \*